United States Patent
Meekins et al.

(10) Patent No.: US 12,424,342 B2
(45) Date of Patent: Sep. 23, 2025

(54) SYSTEMS, DEVICES, AND METHODS FOR BEAM TARGET EXCHANGE AND VOLATILE OBJECT STORAGE

(71) Applicant: TAE Technologies, Inc., Foothill Ranch, CA (US)

(72) Inventors: Michael Meekins, Silverado, CA (US); Jedediah Styron, Mission Viejo, CA (US); Vijay Patel, Eastvale, CA (US); Charles Lee, Irvine, CA (US); Frank Jauregui, Fountain Valley, CA (US); Alain Assaf, Redlands, CA (US); Leslie Webber, Corona, CA (US); Anatoly Muchnikov, Mission Viejo, CA (US); Jon Schroeder, Silverado, CA (US)

(73) Assignee: TAE Technologies, Inc., Foothill Ranch, CA (US)

( * ) Notice: Subject to any disclaimer, the term of this patent is extended or adjusted under 35 U.S.C. 154(b) by 360 days.

(21) Appl. No.: 17/367,004

(22) Filed: Jul. 2, 2021

(65) Prior Publication Data
US 2022/0139585 A1    May 5, 2022

Related U.S. Application Data

(60) Provisional application No. 63/173,275, filed on Apr. 9, 2021, provisional application No. 63/173,285, filed
(Continued)

(51) Int. Cl.
*G21F 5/015* (2006.01)
*A61N 5/10* (2006.01)
*G21F 5/12* (2006.01)

(52) U.S. Cl.
CPC ............... *G21F 5/015* (2013.01); *G21F 5/12* (2013.01); *A61N 5/1077* (2013.01)

(58) Field of Classification Search
CPC ......... G21F 5/015; G21F 5/12; A61N 5/1077; B65D 7/22; B65D 43/161; B65D 43/26; B65D 43/265; B65D 43/267; B65D 43/20
(Continued)

(56) References Cited

U.S. PATENT DOCUMENTS 2,642,541 A * 6/1953 Young .................... G21F 5/015
                                                 976/DIG. 350
4,471,226 A * 9/1984 Wisnosky .............. G21F 5/015
                                                      250/493.1
(Continued)

FOREIGN PATENT DOCUMENTS

CN    111806868 A  * 10/2020
CN    112542258 A  *  3/2021
(Continued)

OTHER PUBLICATIONS

WIPO Application No. PCT/US2021/040345, PCT International Search Report and Written Opinion of the International Searching Authority mailed Dec. 22, 2021.
(Continued)

*Primary Examiner* — Anthony D Stashick
*Assistant Examiner* — Niki M Eloshway
(74) *Attorney, Agent, or Firm* — Alston & Bird LLP

(57) ABSTRACT

Embodiments are provided relating to the exchange of devices or assemblies holding targets used in a beam system. With these embodiments a used target can be rapidly and safely replaced with a new target to permit continued operation in a clinical or other environment. Also provided are embodiments of valves having relatively lower profiles that facilitate engagement and disengagement of beamline sections for access to the target device or assembly. All or a portion of the valve can be part of the target assembly. Also provided are embodiments of storage containers for storing
(Continued)

a volatile object, such as an object comprising a composition sensitive to atmospheric air and/or an object that is radioactive. The storage container can include a two-part shell case assembly configured for housing a volatile object between the two parts, which engage one another to form an air-tight seal therebetween.

20 Claims, 22 Drawing Sheets

Related U.S. Application Data on Apr. 9, 2021, provisional application No. 63/060,831, filed on Aug. 4, 2020, provisional application No. 63/048,633, filed on Jul. 6, 2020.

(58) Field of Classification Search
USPC .................................................. 220/23.87
See application file for complete search history.

(56) References Cited

U.S. PATENT DOCUMENTS

| | | | |
|---|---|---|---|
| 5,523,519 | A | 6/1996 | Weber et al. |
| 9,281,090 | B2 | 3/2016 | Leleu et al. |
| 2006/0011866 | A1 | 1/2006 | Cho |
| 2012/0037629 | A1* | 2/2012 | Morgan .................. G21F 5/12 220/260 |
| 2017/0243666 | A1 | 8/2017 | Azim et al. |
| 2018/0130565 | A1 | 5/2018 | Lehnert et al. |
| 2018/0336974 | A1* | 11/2018 | Heibel .................... G21F 5/015 |
| 2019/0198285 | A1 | 6/2019 | Yahong et al. |

FOREIGN PATENT DOCUMENTS

| | | | |
|---|---|---|---|
| CN | 114023480 | A * | 2/2022 |
| EP | 859370 | A1 * | 8/1998 |
| EP | 0739017 | B1 | 8/1999 |
| EP | 2 612 692 | A1 | 7/2013 |
| FR | 2906638 | A1 * | 4/2008 ............. G21F 5/015 |
| JP | S61-085100 | U | 6/1986 |
| JP | H 08-179093 | A | 7/1996 |
| JP | H 09-5491 | A | 1/1997 |
| JP | 2001 305298 | A | 10/2001 |
| JP | 2001 356200 | A | 12/2001 |
| JP | 2009-32623 | A | 2/2009 |
| JP | 2010-509714 | A | 3/2010 |
| JP | 2015-007535 | A | 1/2015 |
| JP | 2015-528107 | A | 9/2015 |
| JP | 2015-217207 | A | 12/2015 |
| JP | 2017 136651 | A | 8/2017 |
| JP | 2017-521661 | A | 8/2017 |
| JP | 2019-174178 | A | 10/2019 |
| RU | 2298242 | C2 | 4/2007 |
| RU | 128385 | U1 | 5/2013 |
| RU | 2510721 | C1 | 4/2014 |
| RU | 194792 | U1 | 12/2019 |
| RU | 2749909 | C2 | 6/2021 |
| WO | WO 2016/007200 | A1 | 1/2016 |

OTHER PUBLICATIONS

Marks, "Accelerator Magnets," Room Temperature Magnets, CAS Prague 2014, (Jul. 2014).
Taskaev et al., "Vacuum-Insulation Tandem Accelerator for Boron Neutron Capture Therapy," Proceedings of IPAC2011, Spain, CERN, Sep. 2011, p. 3615-3617.
Physical Magnitudes, Handbook edited by I.S. Grigoriev, Moscow, Energoatomizdat, 1991, p. 1171.
Japan Patent Office, Notice of Reasons for Rejection received for Application No. 2023-500026, mailed Feb. 7, 2025, 8 pages, Japan.
English Translation of JP Office Action dated Jun. 18, 2025 for JP Application No. 2023500026, 4 page(s).
JP Office Action Mailed on Jun. 18, 2025 for JP Application No. 2023500026, 4 page(s).

* cited by examiner

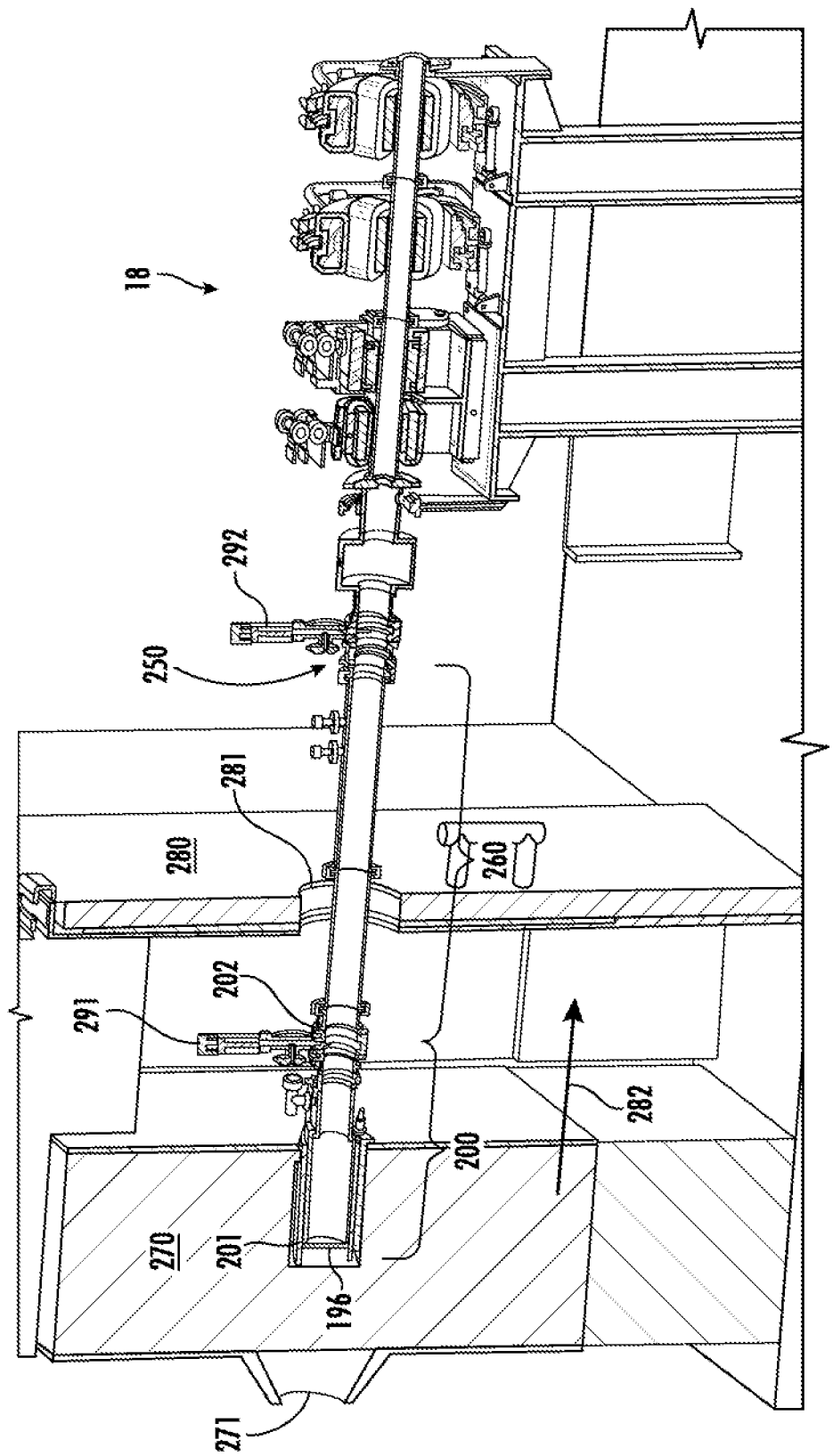

DOOR CLOSED
STOWAGE CONFIGURATION

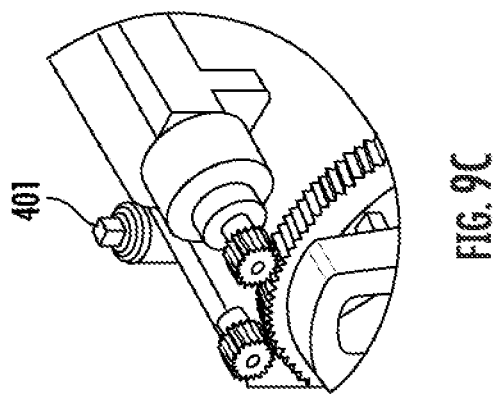
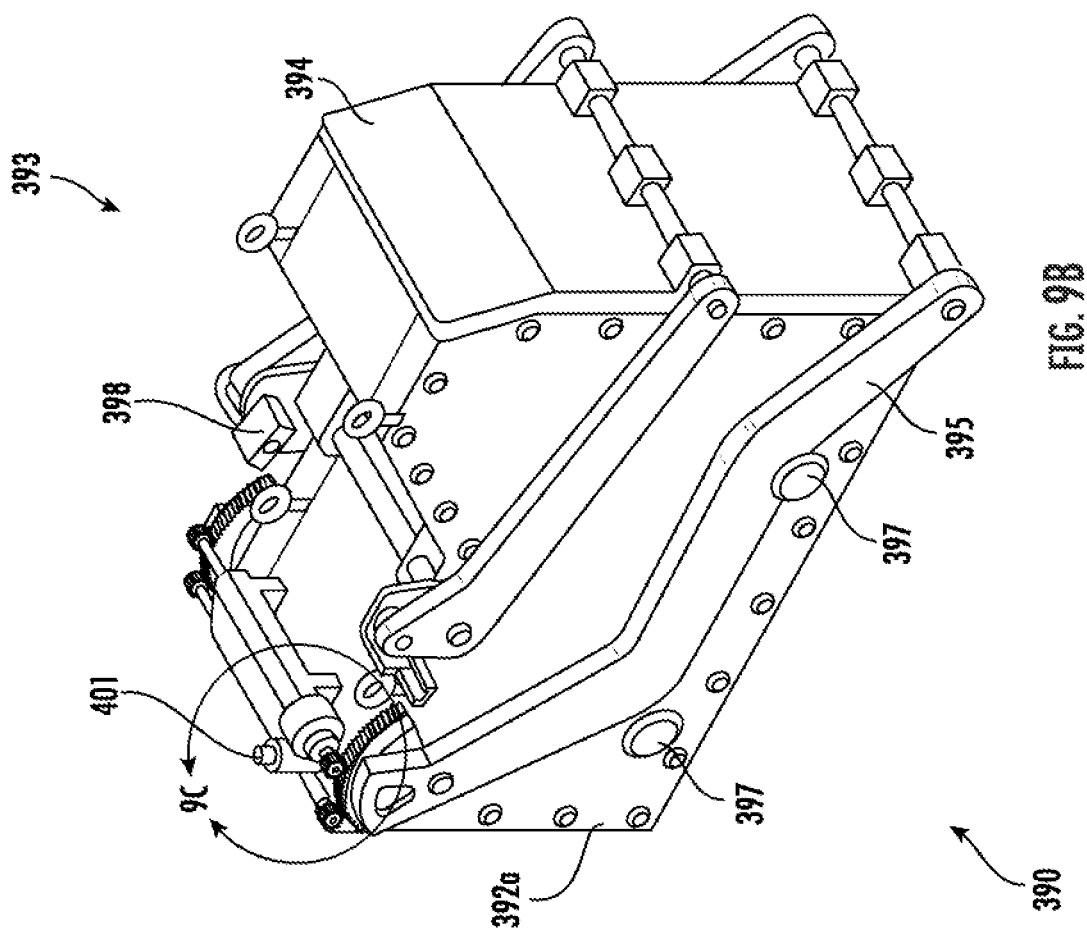

SYSTEMS, DEVICES, AND METHODS FOR BEAM TARGET EXCHANGE AND VOLATILE OBJECT STORAGE

CROSS-REFERENCE TO RELATED APPLICATIONS

This patent application claims priority to U.S. Provisional Patent Appl. Ser. No. 63/048,633, titled "SYSTEMS, DEVICES, AND METHODS FOR BEAM TARGET EXCHANGE," filed Jul. 6, 2020; U.S. Provisional Patent Appl. Ser. No. 63/060,831, titled "SYSTEMS, DEVICES, AND METHODS FOR BEAM TARGET EXCHANGE," filed Aug. 4, 2020; U.S. Provisional Patent Appl. Ser. No. 63/173,275, titled "SYSTEMS, DEVICES, AND METHODS FOR RADIOACTIVE BEAM TARGET STORAGE AND EXCHANGE," filed Apr. 9, 2021; and U.S. Provisional Patent Appl. Ser. No. 63/173,285, titled "SYSTEMS, DEVICES, AND METHODS FOR VOLATILE OBJECT STORAGE," filed Apr. 9, 2021. The contents of all of which are incorporated herein by reference in their entirety for all purposes.

FIELD

The subject matter described herein relates generally to systems, devices, and methods for removing and/or replacing target devices within a beam system and for storing objects that are sensitive to atmospheric conditions, such as objects used during operation of a beam system.

BACKGROUND

Systems that generate energetic particle beams typically include components or devices that receive the beam. These components can be devices used in manipulating or transforming the incoming beam, workpieces altered by the incoming beam, components used for shielding, and others. Depending on the implementation of the beam system, such as the composition and purpose of the receiving device, the type of beam, and the energy of the beam, these components can become radioactive over time and require special handling and/or storage to minimize human exposure.

An example of one such beam system is a neutron beam system used in boron neutron capture therapy (BNCT). Neutron beam systems used for BNCT typically include a target device that, when impacted by a beam of energetic protons, produces a neutron beam that can treat cancerous tumors. The target devices are typically composed of either lithium or beryllium. For example, lithium targets can generate a beam of epithermal neutrons produced via the nuclear reaction $7Li(p,n)7Be$. Target devices are typically integrated into a target assembly that can include secondary structures for supporting use of the target in the overall system, such as a cooling conduit, shielding, structures for engaging and disengaging the assembly, and the like. The target assembly used to generate the neutrons has a finite lifetime and can require multiple replacements annually.

As a by-product of treatment, the target assembly can become radioactive; emitting various gamma rays through a variety of nuclear decay processes that have lifetimes on the order of, e.g., several months. The expected dose to personnel in close proximity to the target assembly, post irradiation, can exceed the allowable annual whole-body dose of 20 millisieverts (mSv), thus making the removal, storage, and/or transportation procedures and any unforeseen maintenance issues challenging.

Reactor-based BNCT systems use similar methods for radioactive material handling as commercial nuclear power plants and the isotope production industry. Examples of these methods include remote handling with mechanical aids or robots, and shielded lifting tables or hoists to move the material to and from the facility to a glove box or a shielding container.

The tools used to handle radioactive material as well as the storage container are built in an arrangement specific to the facility and the metrology of the radioactive material being handled. Incorporation of pre-existing technology, such as those outlined above for reactor-based facilities, would require extensive modification to work with different system designs, such as those configured for accelerator-based BNCT, and the facilities housing such systems. Target handling systems for reactor-based systems are generally not feasible for accelerator-based solutions either due to surface area, volume, mass, or material constraints.

Three general techniques for keeping personnel safe by reducing exposure when removing and handling the irradiated target assembly are: limiting the exposure time, maximizing the distance between the target and personnel, and/or adding copious amounts of gamma shielding between the target and the personnel. These options are, in many cases, not practical and not cost effective. Furthermore, the facility in which the BNCT procedures are performed may have constraints that further limit what solutions are practical and cost effective. Existing solutions for removing and replacing targets generally cannot be satisfactorily applied within many existing safety and facility constraints.

Materials such as magnesium, sodium, and lithium (e.g., materials used in target devices of BNCT systems) are known to be reactive in atmospheric air conditions. These materials are highly volatile, and therefore exposure to even small amounts of oxygen and/or moisture within atmospheric air conditions, such as when assembling target assemblies to be utilized in BNCT systems can cause these materials react to form oxides and/or hydroxides. For applications requiring pure elemental materials, this reaction results in inferior or unusable material properties.

To ensure that air-sensitive materials such as certain highly reactive elemental materials maintain a high purity level during storage and transportation, a need exists for systems and methods for isolating air-sensitive materials and objects from atmospheric conditions.

SUMMARY

Example embodiments of systems, devices, and methods are described herein for the removal of a radioactive component from a beam system, the introduction of a replacement component to the beam system, or both. The embodiments can include a movable device for transporting the component and a guide structure for guiding movement of the movable device. The component can be rapidly, reliably, and efficiently moved from a first position, e.g., an operative position within the beam system, to a second position, e.g., a position within a shielded container to remove the component from the system while minimizing radiation to surrounding personnel.

Embodiments of the components can include a compact valve to maintain a vacuum environment within the component. The valve can have a compact design that permits removal of the component through a minimally sized opening in the adjacent radiation shielding. The compact design also permits the storage container for the component to be kept at a relatively small size. The valve can be readily decoupled from the beamline thereby allowing technical personnel to rapidly exchange the components, such as by placing a used radioactive component within a shielded container and exchanging the used radioactive component for a new component, while minimizing radioactive exposure.

Example embodiments of the component removal system can also be used to introduce a replacement component and thus can accomplish and exchange functionality. Example embodiments of a facility for housing the exchange system are also described herein.

An example shielded container for storing a radioactive component includes an inner container shell. The inner container shell can have multiple inner shell walls collectively defining a first hollow interior for housing the radioactive component. The shielded container can include an outer container shell. The outer container shell can have multiple outer shell walls collectively defining a second hollow interior for housing the inner container shell.

Example embodiments additionally provide for the storage of an object that is sensitive to atmospheric conditions, such as reactive with oxygen, reactive to moisture, and/or the like. In various embodiments, a storage container for storing a volatile object includes a shell case assembly. In various embodiments, the shell case assembly includes a first shell case side and a second shell case side. In some of these embodiments, the shell case assembly defines an exterior surface and an enclosed interior volume defined within an interior portion of each of the first shell case side and the second shell case side and configured for housing a volatile object. In various embodiments, the first shell case side is configured to engage the second shell case side to form an air-tight seal therebetween. In various embodiments, the storage container further includes a coupling device configured to secure the first shell case side with the second shell case side. In various embodiments, the first shell case side includes a vacuum-activated check valve extending therethrough. In various embodiments, the vacuum-activated check valve is configured to open with a lower pressure at the exterior surface of the first shell case side than a pressure at the interior portion of the first shell case side.

Other systems, devices, methods, features and advantages of the subject matter described herein will be or will become apparent to one with skill in the art upon examination of the following figures and detailed description. It is intended that all such additional systems, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIG. 2 is a perspective view depicting an example embodiment of a downstream portion of a neutron beam system.

FIG. 9B is a perspective view of an example embodiment of a shielded container configured to automated operation.

FIG. 9C is a close-up perspective view of a drive mechanism of the shielded container of FIG. 9B.

DETAILED DESCRIPTION

Figure 1A:
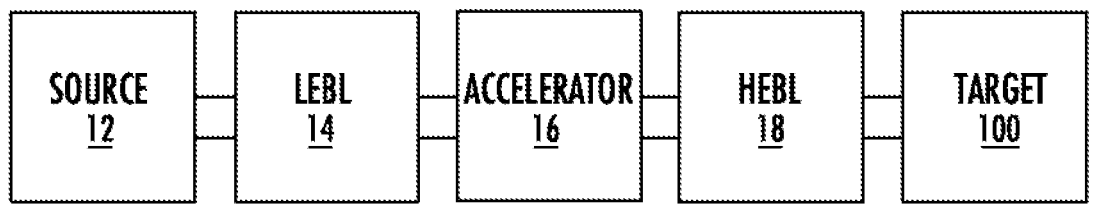
FIG. 1A is a block diagram depicting an example embodiment of a neutron beam system.

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

The term "particle" is used broadly herein and, unless otherwise limited, can be used to describe an electron, a proton (or H+ ion), or a neutron, as well as a species having more than one electron, proton, and/or neutron (e.g., other ions, atoms, and molecules).

The term "atmosphere" or "atmospheric air" is used to refer to components of atmospheric air, including, without limitations, oxygen, moisture (e.g., water vapor, humidity, rain, snow, ice, and/or the like), and/or other components of atmospheric air that are reactive with certain compositions.

Example Implementation Environment

Systems that generate energetic particle beams typically include components or devices that receive the beam. These components can be devices used in manipulating or transforming the incoming beam, workpieces altered by the incoming beam, components used for shielding, and others.

An example of one such beam system is a neutron beam system used in boron neutron capture therapy (BNCT). Neutron beam systems used for BNCT typically include a target device that, when impacted by a beam of energetic protons, produces a neutron beam that can treat cancerous tumors. Example target devices are embodied as metallic (e.g., copper) disks having a layer of either lithium or beryllium on one side thereof. For example, lithium targets can generate a beam of epithermal neutrons produced via the nuclear reaction 7Li(p,n)7Be. Target devices are typically integrated into (e.g., removably integrated into) a target assembly that can include secondary structures for supporting use of the target in the overall system, such as a cooling conduit, shielding, structures for engaging and disengaging the assembly, and the like. Moreover, the target assembly is constructed to maintain ideal environmental conditions in its interior, so as to prevent unwanted decomposition/reaction of the materials of the target device. For example, the target assembly can be sufficiently sealed so as to maintain a vacuum environment or to maintain an inert environment therein. The target assembly used to generate the neutrons has a finite lifetime and can require multiple replacements annually. Therefore, replacement target devices are needed, which must be carefully placed into the target assembly when the lifespan of a used target device has been reached.

As just one example, production of a neutron-producing target device for BNCT encompasses processes for creating a layer of highly pure lithium (e.g., having a thickness of approximately 100 micrometers) onto a surface of a metal (e.g., copper) base plate. The process of applying lithium onto the metal base plate typically requires special coating equipment, and therefore this process is generally performed at a manufacturing facility that is not on-site at a location where the BNCT procedures are performed. However, once the layer of lithium is applied to the metal base plate, the entire target device must be stored and transported until its installation in a target assembly of a BNCT system.

However, lithium can be extremely difficult to handle, because lithium is highly-reactive and corrosive at atmospheric conditions where the material is exposed to air (including oxygen and moisture within the air) at ambient temperatures, such as in general laboratory environments. When exposed to atmospheric air, lithium reacts with oxygen, nitrogen, and humidity within the air to form a nitride and hydroxide-lithium hydroxide (LiOH and LiOH—$H_2O$), lithium nitride ($Li_3N$), and lithium carbonate ($Li_2CO_3$, a result of a secondary reaction between LiOH and $CO_2$), which can delaminate from a metallic substrate in the form of a dust. The air and moisture act as a catalyst for such a series of reactions.

As discussed herein, preserving the layer of lithium, unspoiled and unreacted, in a container with an inert gas or a complete vacuum is an effective method to minimize the potential for exposure to atmospheric air. After application of the lithium (or other highly reactive elemental material to a substrate) under inert gas or vacuum conditions, the resulting target device is placed and sealed into a storage and transport container as discussed herein while remaining under these inert gas or vacuum conditions to maintain the viability of the lithium (or other reactive material) during storage, shipment, and transport.

Example embodiments of systems, devices, and methods are described herein for storage and transportation of manufactured target devices (e.g., manufactured disks having a layer of highly reactive material thereon) within a vacuum or inert gas environment. These systems, devices, and/or methods are be usable with target device removal and/or storage systems and methods corresponding with a beam system that includes a particle accelerator. Target devices utilized in association with particle accelerators are just one example, however embodiments as described herein can be configured for providing storage and transportation solutions for devices including highly reactive materials utilized in other intended applications.

Some example embodiments described herein are examples of systems, devices, and methods for a target removal or exchange system for use with a beam system that includes a particle accelerator.

Particle accelerators are a common example, and the embodiments described herein can be used with any type of particle accelerator or in any particle accelerator application involving production of a charged particle beam at specified energies for supply to the particle accelerator. Example beam systems are suited to provide a negative particle beam to a tandem accelerator, but this is just an example type of accelerator. The embodiments described herein can be utilized with: beam systems used as scientific tools, such as for nuclear physics research; beam systems used in industrial or manufacturing processes, such as the manufacturing of semiconductor chips; accelerators for the alteration of material properties (such as surface treatment); beam systems for the irradiation of food; and beam systems for pathogen destruction in medical sterilization. The embodiments can also be used in combination with imaging applications, such as cargo or container inspection. And by way of another non-exhaustive example, the embodiments can be used in combination with beam systems for medical applications, such as medical diagnostic systems, medical imaging systems, or radiation therapy systems. Again however, use of various embodiments in association with beam systems is just one example, and other embodiments can be configured for use in association with other industries, such as the manufacture of lithium-ion batteries, and/or other industrial applications requiring storage and/or transportation of materials that are highly reactive under atmospheric conditions.

For context, one application of embodiments as discussed herein is the storage and transport of target devices utilized in a radiation therapy system such as a BNCT system. For ease of description, many embodiments described herein will be done so in the context of a neutron beam system for use in BNCT, although the embodiments are not limited to just neutron beams nor BNCT applications.

Example BNCT Applications

Turning in detail to the figures, FIG. 1A is a schematic diagram of an example embodiment of a beam system 10 for use with embodiments of the present disclosure. In FIG. 1A, beam system 10 includes a source 12, a low-energy beamline (LEBL) 14, an accelerator 16 coupled to the low-energy beamline (LEBL) 14, and a high-energy beamline (HEBL) 16 extending from the accelerator 16 to a target 100. LEBL 14 is configured to transport a beam from source 12 to an input of accelerator 16, which in turn is configured to produce a beam by accelerating the beam transported by LEBL 14 HEBL 18 transfers the beam from an output of accelerator 16 to target 100. Target 100 can be a structure configured to produce a desired result in response to the stimulus applied by the incident beam, or can modify the nature of the beam. Target 100 can be a component of system 10 or can be a workpiece that is conditioned or manufactured, at least in part, by system 10.

Figure 1B:
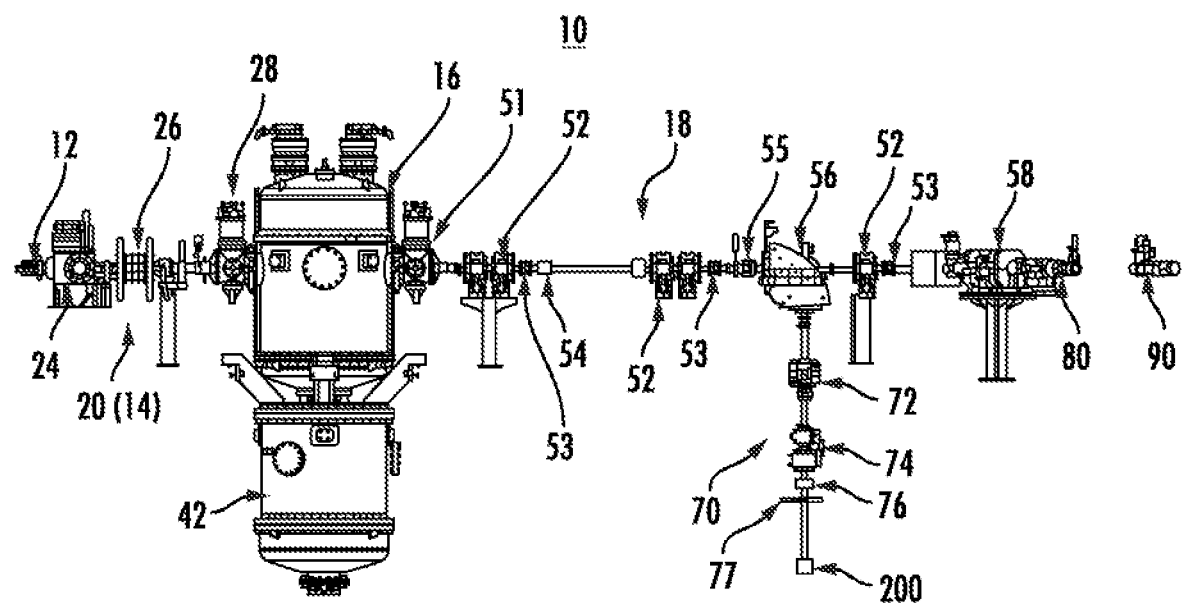
FIG. 1B is a schematic diagram depicting another example embodiment of a neutron beam system.

FIG. 1B is a schematic diagram illustrating another example embodiment of a neutron beam system 10 for use in boron neutron capture therapy (BNCT). Here, source 12 is an ion source and accelerator 16 is a tandem accelerator. Neutron beam system 10 includes a pre-accelerator system 20, serving as a charged particle beam injector, high voltage (HV) tandem accelerator 16 coupled to pre-accelerator system 20, and HEBL 18 extending from tandem accelerator 16 to a neutron target assembly 200 housing target 100 (not shown). In this embodiment target 100 is configured to generate neutrons in response to impact by protons of a sufficient energy, and can be referred to as a neutron generation target. Neutron beam system 10 as well as pre-accelerator system 20 can also be used for other applications such as those other examples described herein, and is not limited to BNCT.

Pre-accelerator system 20 is configured to transport the ion beam from ion source 12 to the input (e.g., an input aperture) of tandem accelerator 16, and thus also acts as LEBL 14. Tandem accelerator 16, which is powered by a high voltage power supply 42 coupled thereto, can produce a proton beam with an energy generally equal to twice the voltage applied to the accelerating electrodes positioned within accelerator 16. The energy level of the proton beam can be achieved by accelerating the beam of negative hydrogen ions from the input of accelerator 16 to the innermost high-potential electrode, stripping two electrons from each ion, and then accelerating the resulting protons downstream by the same applied voltage.

HEBL 18 can transfer the proton beam from the output of accelerator 16 to the target within neutron target assembly 200 positioned at the end of a branch 70 of the beamline extending into a patient treatment room. System 10 can be configured to direct the proton beam to any number of one or more targets and associated treatment areas. In this embodiment, the HEBL 18 includes three branches 70, 80 and 90 that can extend into three different patient treatment rooms, where each branch can terminate in a target assembly 200 and downstream beam shaping apparatus (not shown). HEBL 18 can include a pump chamber 51, quadrupole magnets 52 and 72 to prevent de-focusing of the beam, dipole or bending magnets 56 and 58 to steer the beam into treatment rooms, beam correctors 53, diagnostics such as current monitors 54 and 76, a fast beam position monitor 55 section, and a scanning magnet 74.

The design of HEBL 18 depends on the configuration of the treatment facility (e.g., a single-story configuration of a treatment facility, a two-story configuration of a treatment facility, and the like). The beam can be delivered to target assembly (e.g., positioned near a treatment room) 200 with the use of bending magnet 56. Quadrupole magnets 72 can be included to then focus the beam to a certain size at the target. Then, the beam passes one or more scanning magnets 74, which provides lateral movement of the beam onto the target surface in a desired pattern (e.g., spiral, curved, stepped in rows and columns, combinations thereof, and others). The beam lateral movement can help achieve smooth and even time-averaged distribution of the proton beam on the lithium target, preventing overheating and making the neutron generation as uniform as possible within the lithium layer.

After entering scanning magnets 74, the beam can be delivered into a current monitor 76, which measures beam current. Target assembly 200 can be physically separated from the HEBL volume with a gate valve 77. The main function of the gate valve is separation of the vacuum volume of the beamline from the target while loading the target and/or exchanging a used target for a new one. In embodiments, the beam may not be bent by 90 degrees by a bending magnet 56, it rather goes straight to the right of FIG. 1B, then enters quadrupole magnets 52, which are located in the horizontal beamline. The beam could be subsequently bent by another bending magnet 58 to a needed angle, depending on the building and room configuration. Otherwise, bending magnet 58 could be replaced with a Y-shaped magnet in order to split the beamline into two directions for two different treatment rooms located on the same floor.

FIG. 2 is a perspective view of an example embodiment of a downstream portion of beam system 10 configured for use in a BNCT procedure. Here, a portion of HEBL 18 is shown with an adjustable length device 250. Adjustable length device 250 can be configured to alter or adjust its length along the beam axis to permit components to be removed or added from the beam line. In this embodiment, adjustable length device 250 is configured to expand and contract along the beam axis, and is configured structurally as a bellows.

HEBL 18 includes a removable line section (e.g., a spool) 260 that is removable for maintenance or other purposes. Line section 260 is in turn connected to target assembly 200, which carries the neutron generating target device 196 at or near the assemblies downstream end 202 (e.g., forming the downstream terminus of the assembly). Target assembly 200 is at least partially housed within a beam shaping assembly (or apparatus) (BSA) 270. BSA 270 can be configured to moderate the energies of neutrons in the neutron beam produced by the target to an optimal level for clinical use, shape the neutron beam for focused propagation to the patient from BSA output 271 (e.g., with the use of shielding and reflectors) and otherwise customize or configure the neutron beam for optimal use in the BNCT procedure. One or more retractable radiation shields 280 can be positioned between target assembly 200 and HEBL 18. Here, two shields 280 (one is shown) can slide together using a roller track or other mechanism. The two shields 280 can come together and form an aperture 281 (e.g., in a closed shape like a circle, ellipse, square, or the like) that can surround line section 260 and permit line section 260 to pass through shielding 280. Retraction of shields 280 can allow line section 260 to be removed, which in turn can permit target assembly 200 to be removed from BSA 270 (e.g., by retracting in an upstream direction 282) for purposes of maintenance or replacement with a new target assembly, as described below.

A valve 291 is present at or near an upstream end 201 of target assembly 200. Valve 291 can be placed in an open state to allow a charged particle beam to pass during operation of system 10 where the interior of HEBL 18 is in a vacuum (near vacuum) state. To maintain the vacuum state and prevent expulsion of radioactive materials, valve 291 is closed during disassembly of HEBL 18 maintenance or target exchange. Another valve 292 is present upstream of line section 260, which also is kept in an open state during operation and then closed to maintain a vacuum state within HEBL 18 and permit removal of line section 260. In this example, valves 291 and 292 are configured as gate valves with a sealing wall that is raised to open the valve and lowered for closure, however other valve configurations can be used including the compact valve configurations described elsewhere herein.

Removal and exchange of a target assembly 200 can be performed via any of a variety of methodologies and corresponding mechanisms. For example, a target exchange system encompasses a series of rails or other guide structures and containers to facilitate positioning of the target assembly within the HEBL 18, and to facilitate removal of the target assembly from the HEBL 18, so as to minimize the potential radiation exposure risk to a technician when disconnecting the target assembly 200 from the HEBL 18 and guiding the radioactive target assembly 200 into a shielded container for storage while the radiation emission from the target assembly 200 disseminates. The target exchange system can be specifically configured for placement of the target assembly 200 within a shielded container with such an orientation as to facilitate access to a downstream end 202 of the target assembly 200, to enable access to the enclosed target device 196 therein (so as to facilitate replacement thereof). Access to the target assembly 200 within the shielded container may be limited while the radioactivity of the target assembly 200 diminishes, and therefore the shielded container can be easily sealed to impede radiation leakage while the level of radioactivity of the target assembly 200 decreases.

However, in other embodiments, the target assembly 200 can simply remain within (and remain sealed within) the shielded container until levels of radioactivity decrease to a level safe for handling by a technician, and the target assembly 200 can then be manually removed from the shielded container and moved to an inert environment or a vacuum environment (with negligible atmospheric air content), such as within an enclosed and seal glovebox, where the target assembly 200 can be disassembled for removal and replacement of the included target device 196.

FIGS. 3A-3D are perspective views depicting an example embodiments of a target exchange system 300 for use with neutron beam system 10 and to facilitate placement within a shielded container 390. System 300 can include one or more guide structures that guide the movement of target assembly 200 from its operative position within BSA 270 to an extracted position within a shielded container 390 (FIG. 3D), or alternatively a new target assembly 200 can be removed from a carrying container and introduced into BSA 270 in opposite fashion. System 300 thus permits the removal of a used (radioactive) target assembly 200 (or other system component), the insertion or introduction of a new target assembly 200, or both (exchange of target assemblies).

The removal guide structures can be configured as one or more tracks, channels, passageways, struts, rails, conduits, or other structures that can be fixed in place and interface with the target assembly 200 (or other radiation receiving device or component), or a mechanism coupled with the target assembly 200 (e.g., such as a carriage, carrier, conveyor, or cart) to guide the movement of the target assembly from within or near BSA 270 to the shielded container 390. In some embodiments the movement of target assembly 200 is restricted to only that which is permitted by the guide structures.

In this embodiment, target exchange system 300 includes two tracks adapted to receive wheels of a carriage that is configured to hold and/or carry assembly 200. For example, the track can include a recessed space that holds the wheels and permits rotation of the wheels along the recessed space in the direction of the track. Target assembly 200 can be moved or slid along the tracks from one position to another. The movement can be manually actuated (such as pushing and/or pulling by a technician) or actuated automatically such as with a motorized carriage, with electromagnetic force, with pneumatic devices, with one or more robotic arms, and/or the like.

Here, the carriage (obscured within tracks) is mounted directly to target assembly 200. Adjustable length device 250 can be extended and retracted to cause or enable movement of target assembly 200. As device 250 is extended, target assembly 200 can be inserted into BSA 270 (FIG. 2), which can be installed in a permanent or semi-permanent fashion that is relatively more difficult to remove and/or replace as compared to target assembly 200. As device 250 is retracted the target assembly 200 can move from within BSA 270 to shielded container 390. In some embodiments, line section 260 may need to be removed, although this may not be necessary depending on the configuration of system 300.

The tracks can include multiple sections or portions 302, 304, 306, and 308. Track section 302 is adjacent BSA 270. A downstream end or terminus of section 302 can extend into BSA 270 as shown, or can cease just outside of BSA 270. The orientations of the track sections 302-308 with respect to each other can vary in any desired manner to assist in movement of target assembly 200 between BSA 270 and container 390. Track sections 302-308 can be supported by a stand or group of legs 310. Track sections 302-308 can be configured as rigid supports that accept the weight of the target assembly 200 and carriage and thus can be positioned without the need for additional supports. Track sections 302-308 and system 300 as a whole can be composed of materials that do not readily become radioactive in the presence of the radiation generated by system 10, e.g., nuclear friendly materials, and thus can minimize introduction of additional radiation.

FIGS. 3A-3D depict one example embodiment that is usable in combination with a shielded container 390 as discussed herein, although other configurations are permitted. In the embodiment of FIGS. 3A-3D, track section 302 extends along the beam axis or upstream-downstream axis (e.g., an axis that permits movement in an upstream or downstream direction). In this embodiment section 302 extends in a horizontal or substantially horizontal fashion, although deviation from the horizontal is permitted. Track section 302 extends through aperture 281 of shields 280. Track section 302 transitions to track section 304 which is curved (e.g., has a radius of curvature) or bent, and track section 304 transitions to upper track section 306 which is relatively straight. Upper track section 306 transitions to lower track section 308, which is also straight and leads to a space 312 where shielded container 390 can be placed. Upper section 306 and lower section 308 are oriented along an axis that is transverse (e.g., at an angle with respect to) to the axis of section 302. This axis of sections 306, 308 can be along the direction of gravity (up and down) as depicted here, or can be laterally oriented (e.g., side to side) or any combination thereof. In this embodiment sections 306, 308 extend in a vertical or substantially vertical fashion, although deviation from the vertical is permitted. The change in axes between section 302 and sections 306, 308 will determine the amount of curvature present in section 304.

Figure 3A:
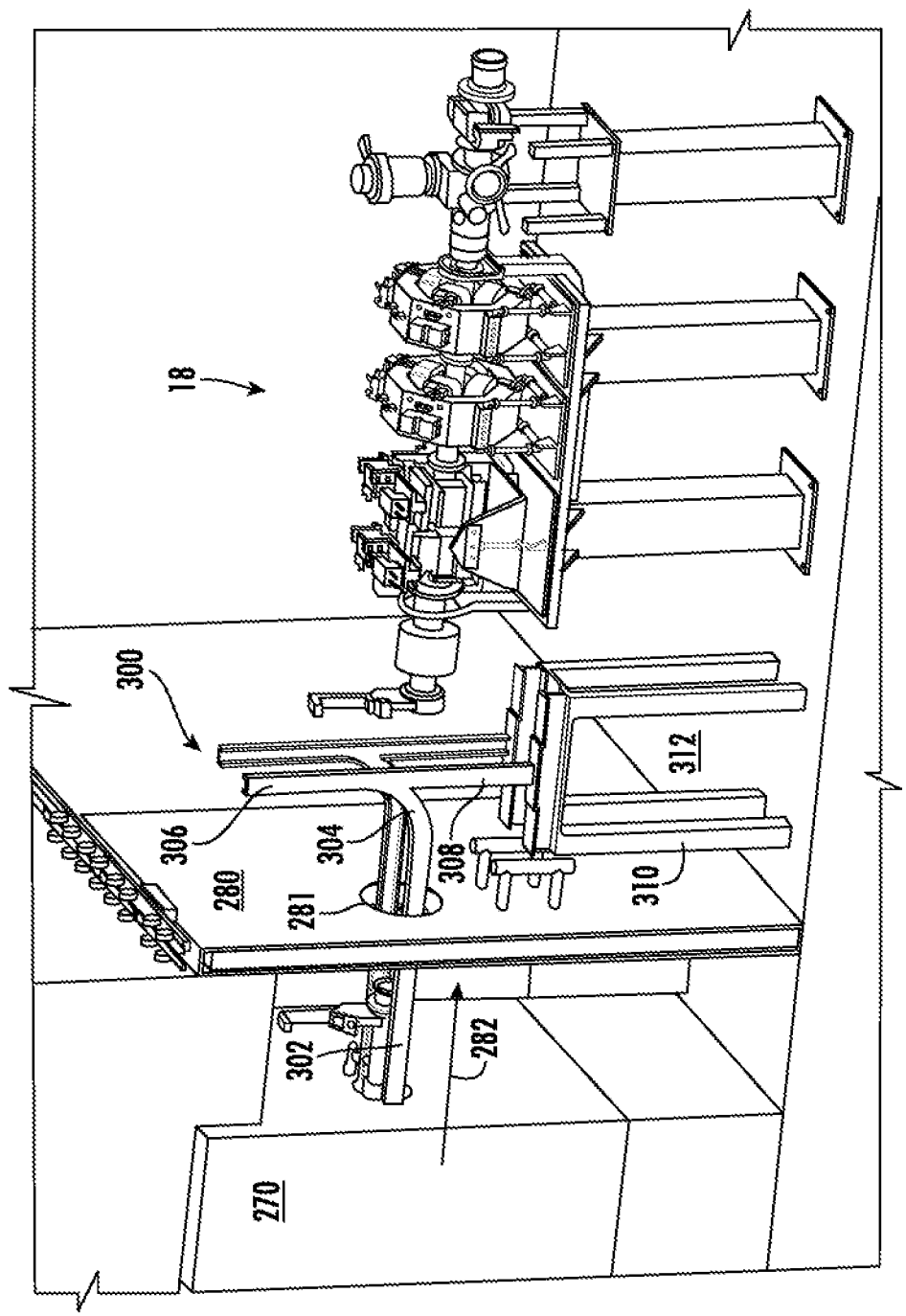
FIGS. 3A-3D are perspective views depicting an example embodiment of a target exchange system at various stages of use to remove a target assembly from an example neutron beam system.
Figure 3B:
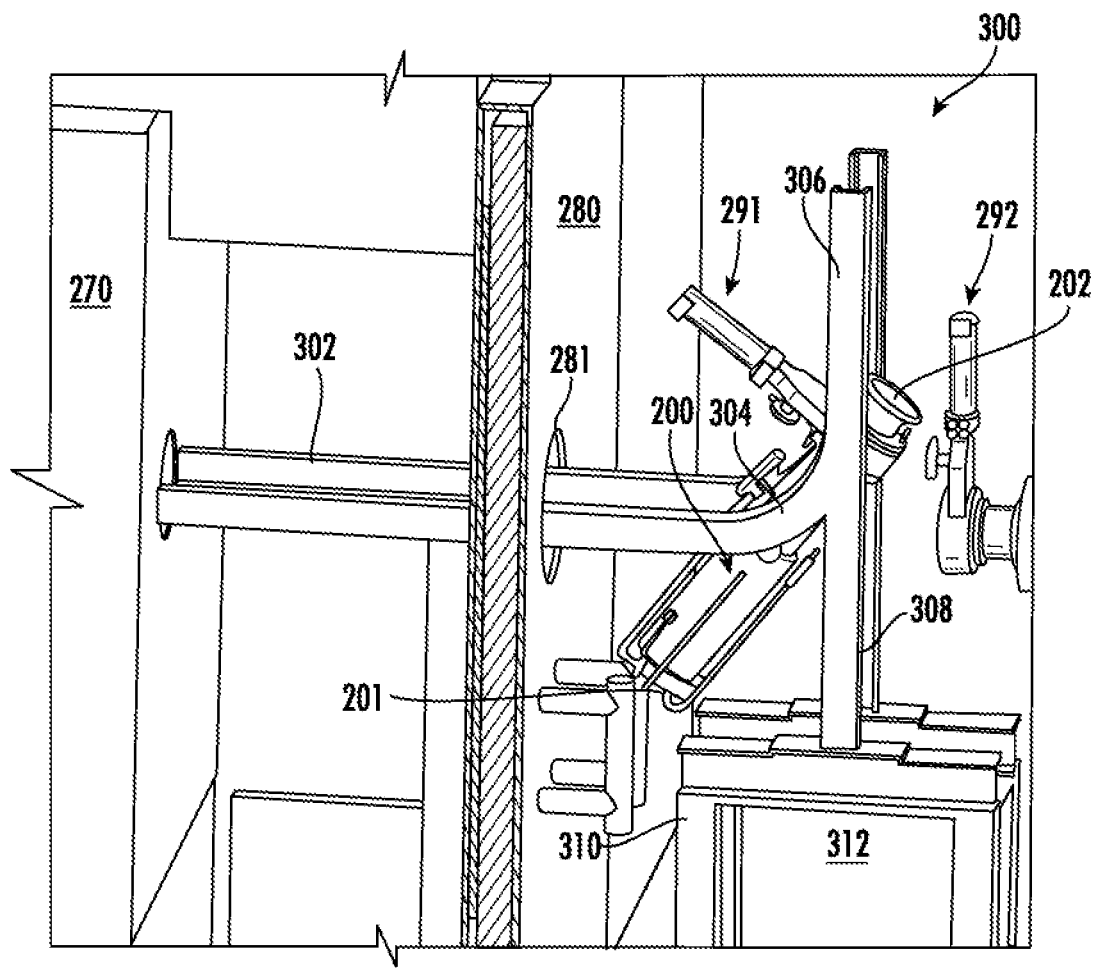

FIG. 3A depicts target assembly 200 partially removed from BSA 270. Target assembly 200 has been moved along track section 302 in upstream direction 282. In FIG. 3B, target assembly 200 has been moved from section 302 into section 304, and the orientation of target assembly 200 changes to follow the orientation of the track sections, e.g., from an upstream-downstream orientation towards an increasingly transverse orientation. The carriage (obscured by tracks) is located between the midpoint and downstream end 202 of target assembly 200. Thus, as target assembly 200 moves along track section 304, upstream end 201 pivots to a position in close proximity with space 312 where shielded container 390 (FIG. 3D) is placed. This allows the portion of target assembly 200 carrying target 196 to be placed into shielded container 390 first, and thus minimizes the amount of time that the most radioactive portion of target assembly 200 is exposed to the environment and any personnel within range.

Figure 3C:
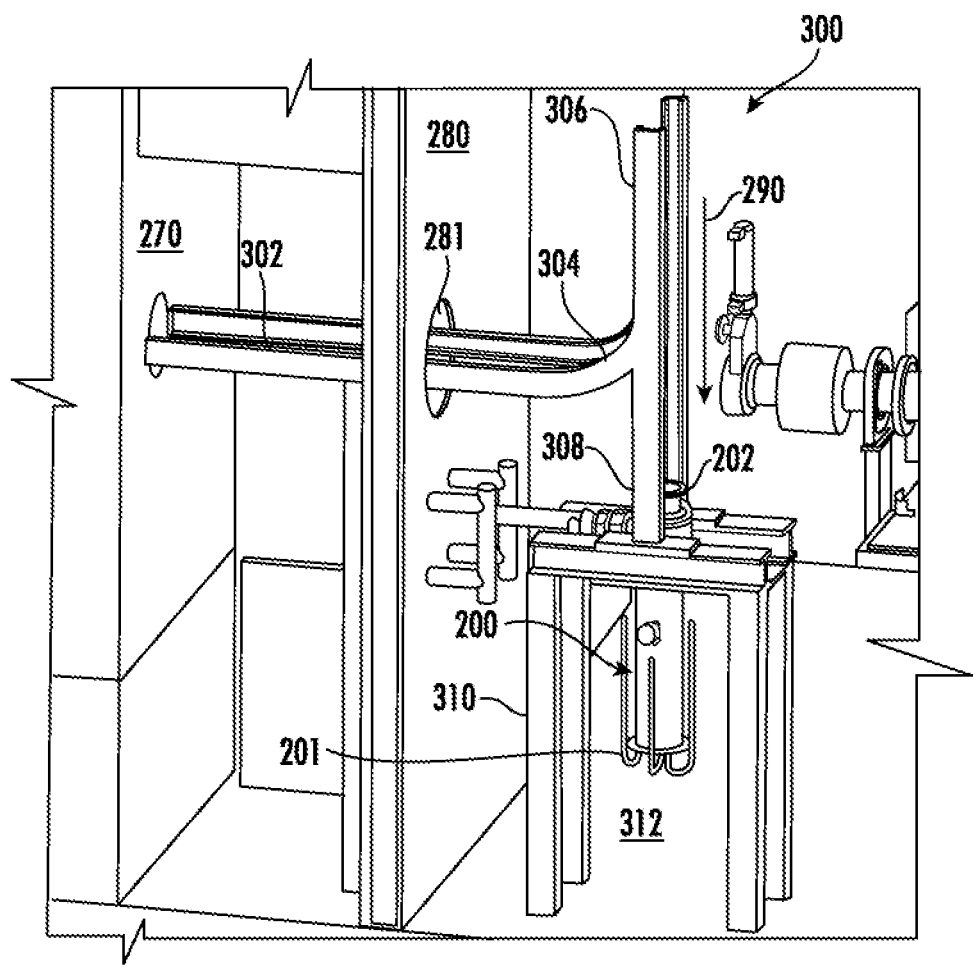
Figure 3D:
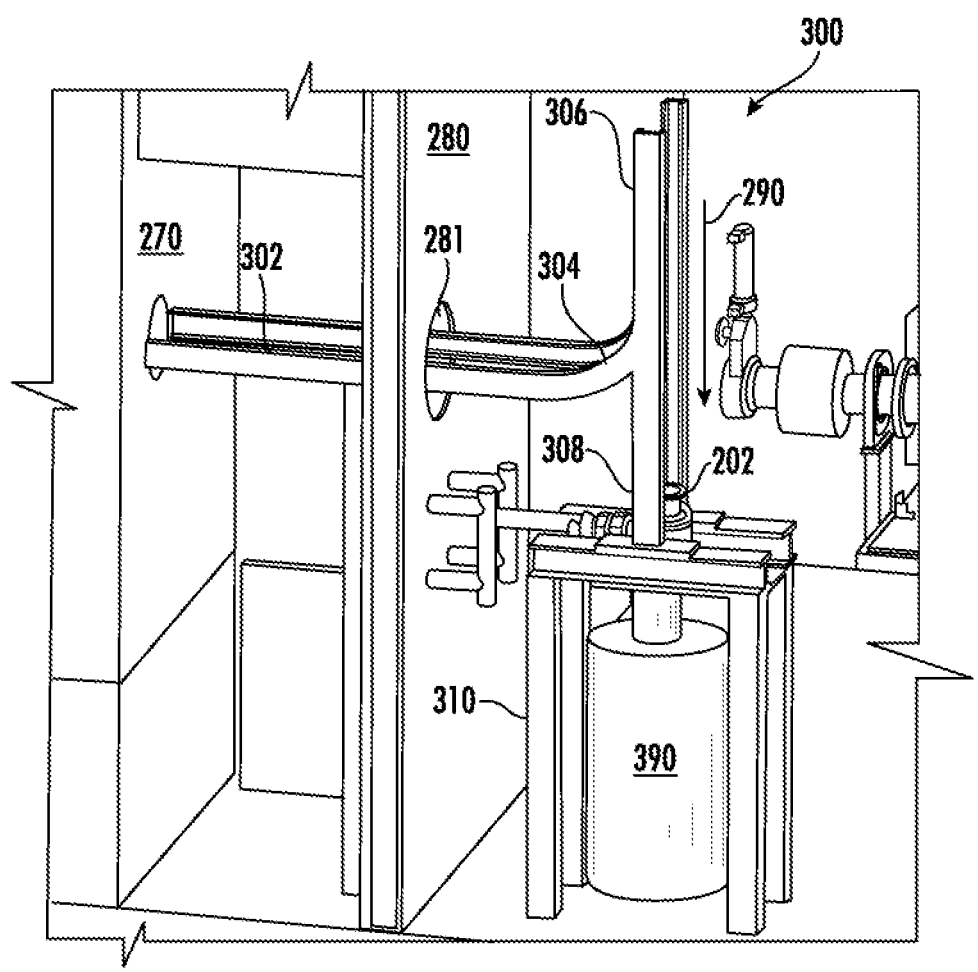

Continued movement of target assembly 200 from section 304 to upper section 306 completes the change in orientation of target assembly 200 to the vertical orientation. Movement of target assembly downwards in direction 290 from upper track section 306 to lower track section 308 moves target assembly into a position within space 312 as depicted in FIG. 3C. This position is shown again in FIG. 3D except with the presence of shielded container 390. Target assembly 200 can be loaded directly into container 390 with the carriage attached and then container 390 can be closed and sealed to minimize the amount of time assembly 200 is exposed in the ambient environment. Thus lower track section 308 can have an open terminus at the bottom that permits the carriage to slide directly out of tracks 308 and into container 390. In other embodiments a latch, removable or releasable guard or stop, or other mechanism can be present to prohibit target assembly 200 from dropping out of tracks prematurely.

Figure 4A:
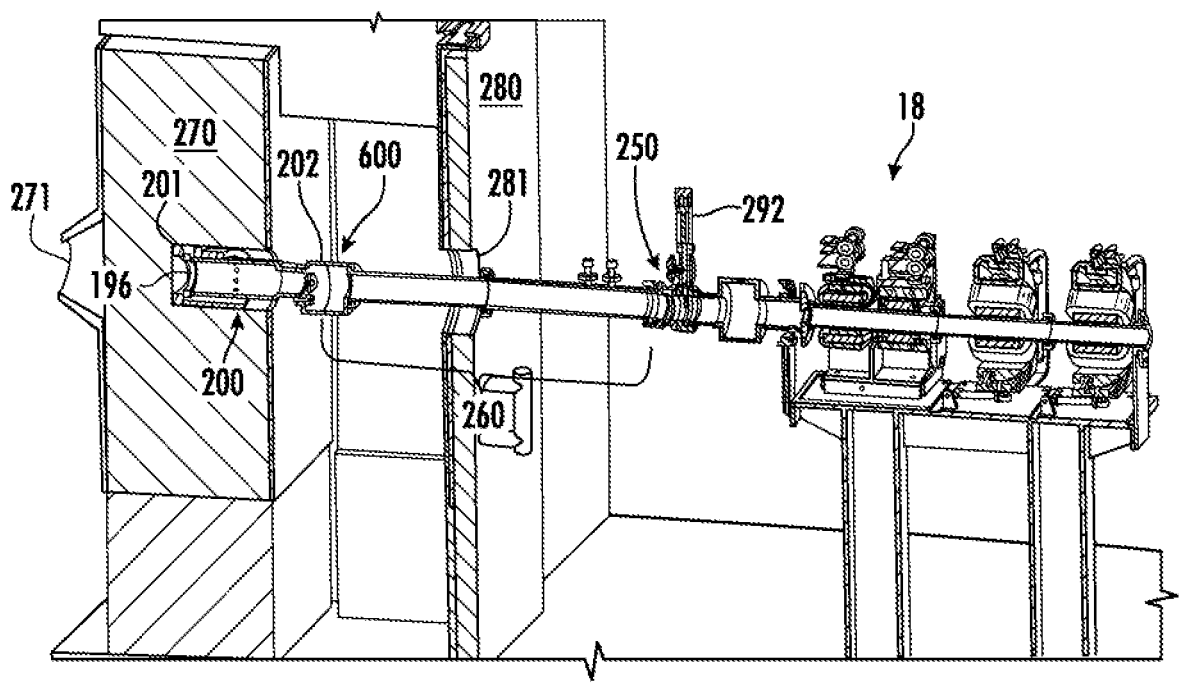
FIG. 4A is a partial cross-sectional view of an example embodiment of a beamline within a boron neutron capture therapy (BNCT) facility.

FIG. 4A depicts another example embodiment of HEBL 18 portion of system 10 within a BNCT treatment facility. This embodiment utilizes a compact valve assembly 600 at the upstream end 201 of target assembly 200. Compact valve assembly 600 enables quicker disassembly of line section 260 from target assembly 200, and also enables technical personnel to place greater reliance on shielding 280 during the exchange process. Valve assembly 600 is described in greater detail with respect to FIGS. 6A-6D.

Figure 5A:
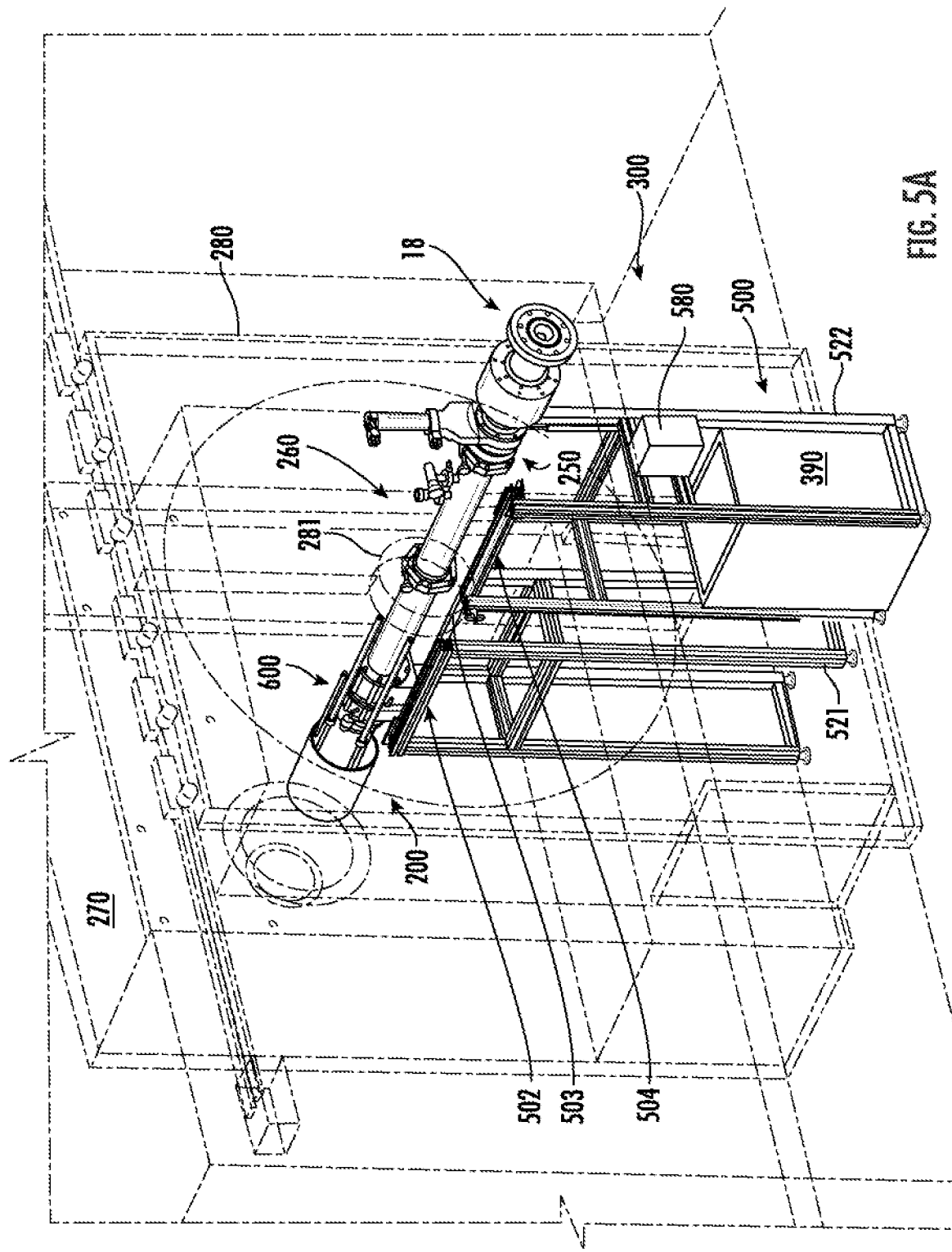
FIGS. 5A-5E are perspective views of example embodiments of a beamline and target exchange system during various stages of disassembly and target exchange.
Figure 5B:
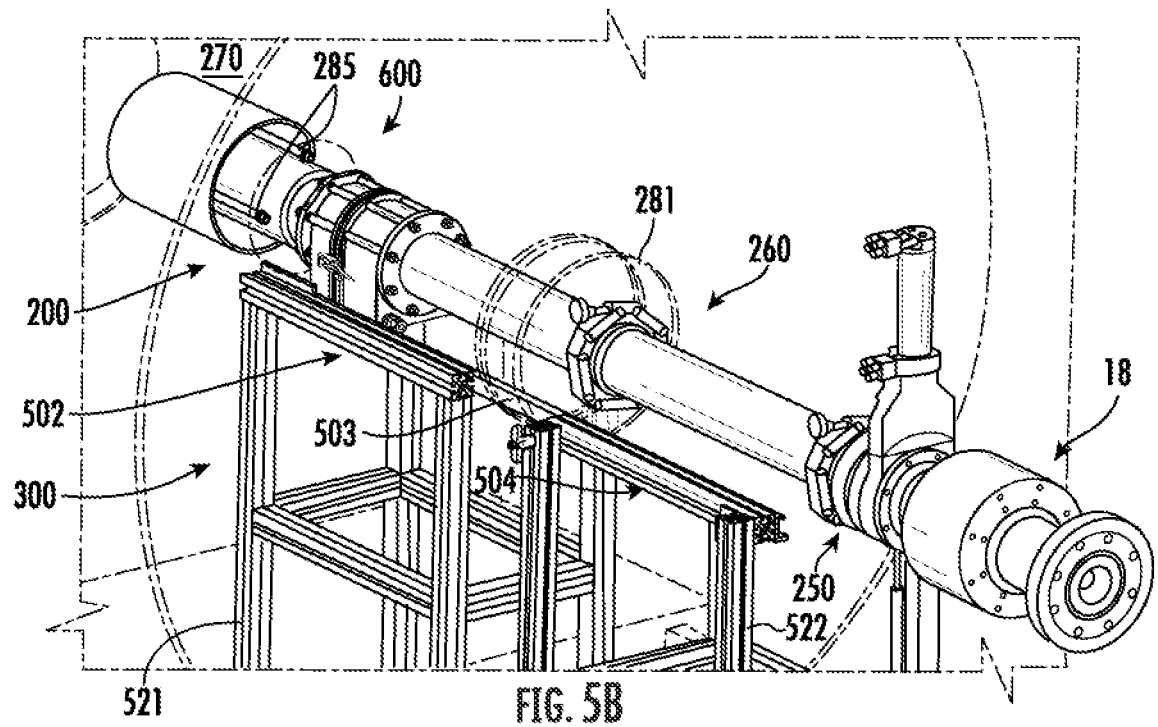

FIGS. 5A-5G are an assortment of views depicting another example embodiment of target exchange system 300. FIG. 5A is a partial cross-sectional and perspective view depicting target assembly 200 within BSA 270 prior to removal with the aid of target exchange system 300. Various other aspects of system 10 and HEBL 18 are omitted for clarity. FIG. 5B is an enlarged view of a portion of FIG. 5A showing assembly 200 and aspects of system 300 in greater detail.

In this embodiment system 300 includes a support 500 with a downstream portion 521, located between BSA 270 and radiation shields 280, and an upstream portion 522 located on the upstream side of shields 280. Support 500 can have one or more guide structures to guide movement of target assembly 200 into position over and into container 390. Here, support 500 has guide structures on opposite sides of assembly 200, where each guide structure includes guide sections 502, 504. Sections 502, 504 include struts of support 500 coupled with tracks 503, 505 (respectively) for interfacing with a carriage 602 (FIG. 6A) of assembly 200. While described as a track in this embodiment, the portion of the guide structure that interfaces with carriage 602 can be configured as a channel, passageway, strut, rail, conduit, or other structure. Track 503 extends between the two support portions through aperture 281 of shields 280. Instead of continuously moving assembly 200 along the guide structure to reorient assembly 200 for insertion into container 390, this embodiment incorporates a reorientation capability that permits the orientation of target assembly 200 to be changed without motion along the guide structure track. Reorientation of assembly 200 can occur in various ways, and in this example is accomplished by altering the orientation of section 504 through a pivot or rotation movement.

Figure 4B:
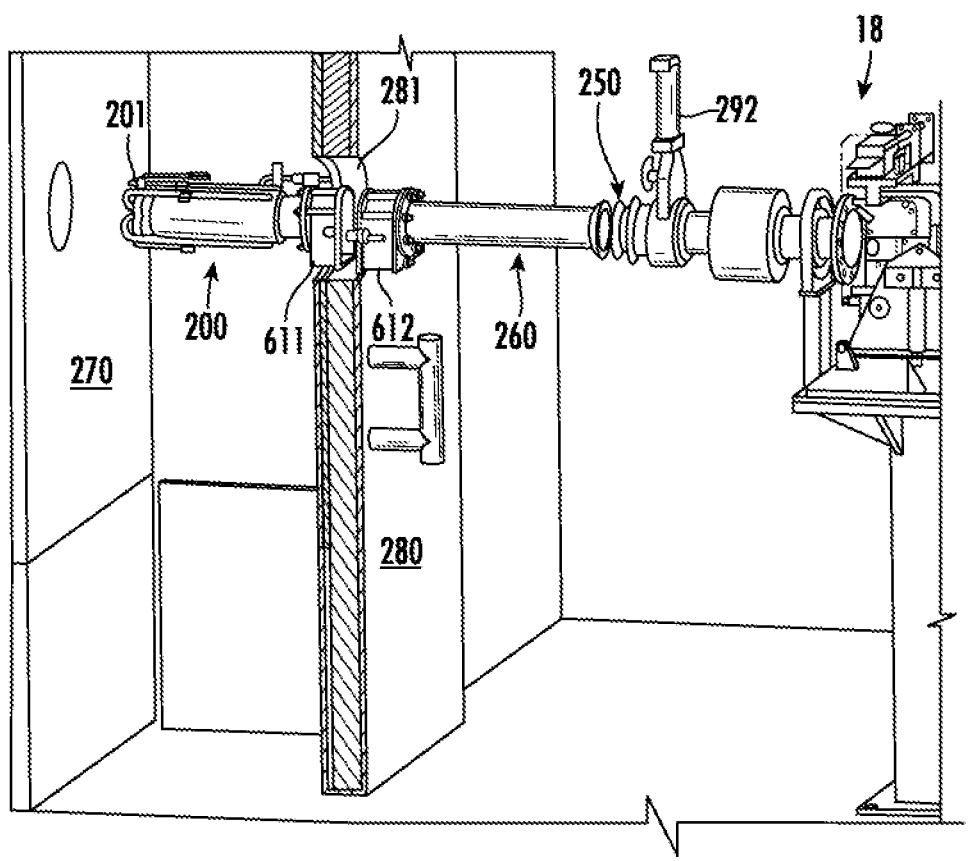
FIG. 4B is a partial cross-sectional view of an example embodiment of the beamline during disassembly.
Figure 5C:
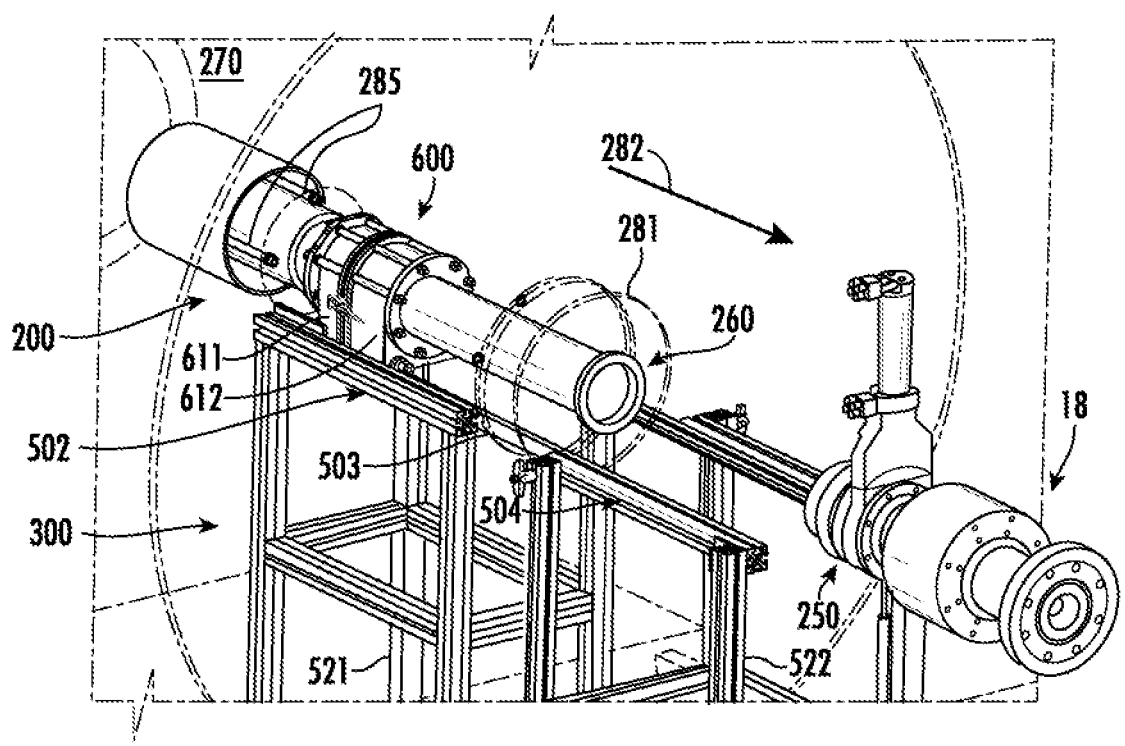

When beginning disassembly of HEBL 18, valves 600 and 292 are transitioned from the open to the closed positions. Adjustable length device 250 can then be disconnected from line section 260 and shortened to permit removal of at least a portion of line section 260. FIG. 5C depicts HEBL 18 after device 250 has been retracted and a portion of line section 260 has been disconnected and removed. Assembly 200 is now free to travel along track section 502 through aperture 281 in upstream direction 282, to a position where the remainder of line section 260 is accessible on the upstream side of aperture 281. Coolant lines 284 (shown in partial section) can be removed from target assembly 200. The remaining line section 260 is coupled with an upstream housing 612 of valve 600, and these can be decoupled from a downstream housing 611 of valve 600 and removed. Valve 600 as described in more detail with respect to FIGS. 6A-6D. FIG. 4B depicts HEBL 18 after decoupling of housings 611 and 612 of valve 600.

Figure 5D:
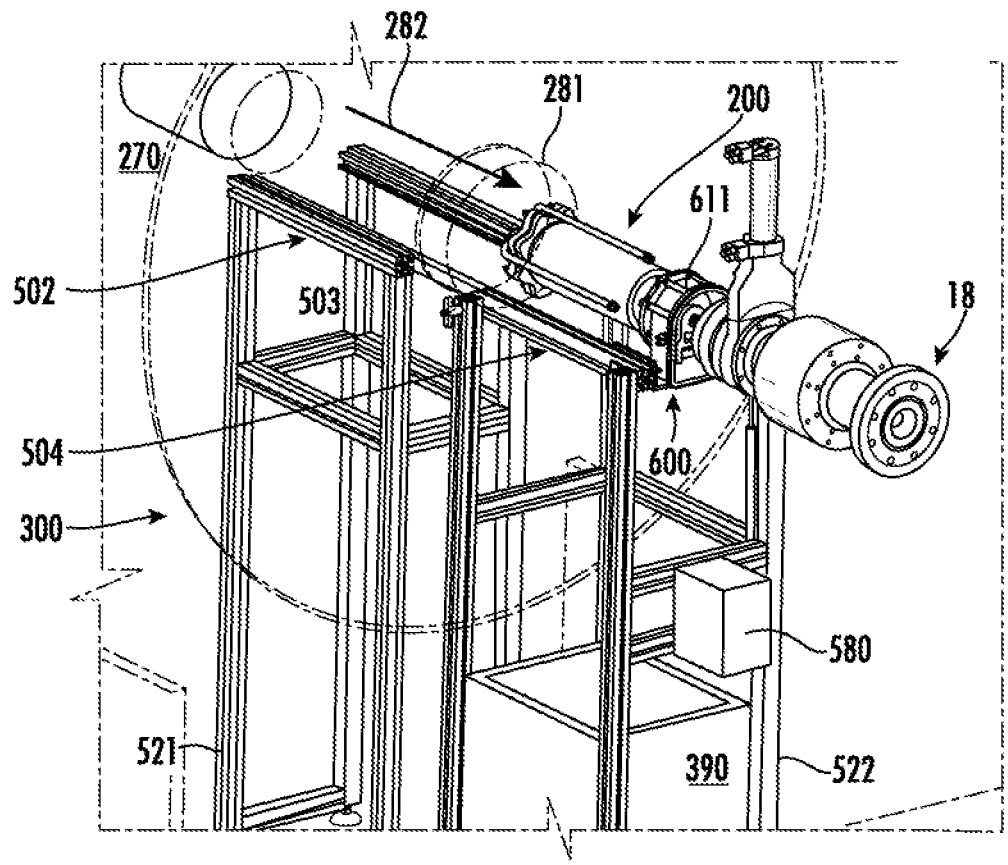
Figure 5E:
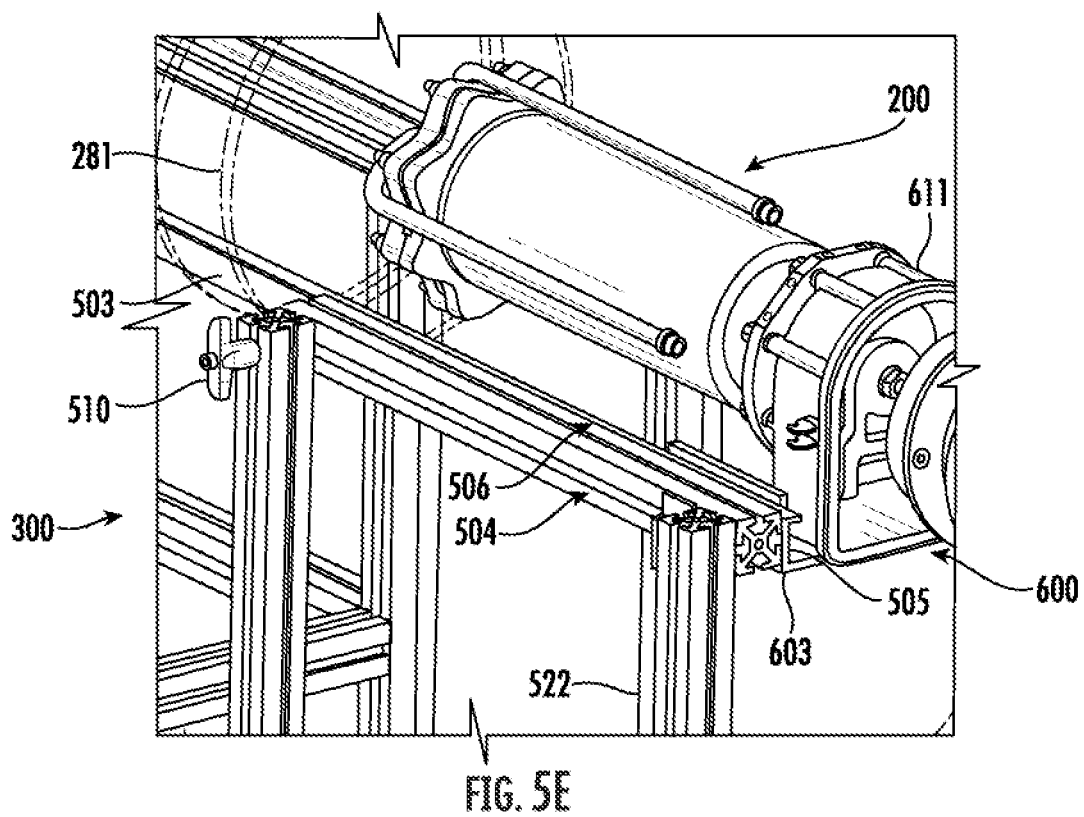

Assembly 200 can then be moved further in upstream direction 282 from track 503 to track 505 of guide section 504, where assembly 200 can be moved into the fully retracted position depicted in FIG. 5D. The interface between track 503 and track 505 is indicated by 506. FIG. 5E depicts assembly 200 in this fully retracted position in greater detail. Stop members can be present on track section 504 to stop travel of assembly 200 at the position of full retraction. Assembly 200 can be locked in this fully retracted position in track 505 to prevent movement during reorientation.

Assembly 200 can then be re-oriented for insertion into container 390. The reorientation of assembly 200 is described with respect to FIG. 5F, which is a perspective view of the upstream portion 502 of support 500, and FIG. 5G, which is a side view depicting system 300 after reorientation of assembly 200.

Each guide section 504 (including the horizontal support strut and track 505) is pivotably or rotatably coupled with a vertical support strut of support 500 by way of a hinge 508. Guide sections 504 can be locked in the horizontal position (FIGS. 5A-5E) by way of a lock mechanism 510. In this embodiment, each lock mechanism 510 is configured as an actuatable release pin. In other embodiments, a single lock mechanism 510 can be used to lock both guide sections 504 in position, thereby only requiring one act of disengagement to release both sections 504. Each guide section 504 is coupled with a bias member 512 that is biased to resist reorientation. Disengagement of lock mechanism 510 frees guide section 504 pivot. This pivoting motion is dampened by bias member 512, which in this embodiment is configured as a gas-biased dampening spring, to facilitate control of the reorientation. Other structures can be used as bias member 512, such as helical or torsion springs and the like.

Figure 5G:
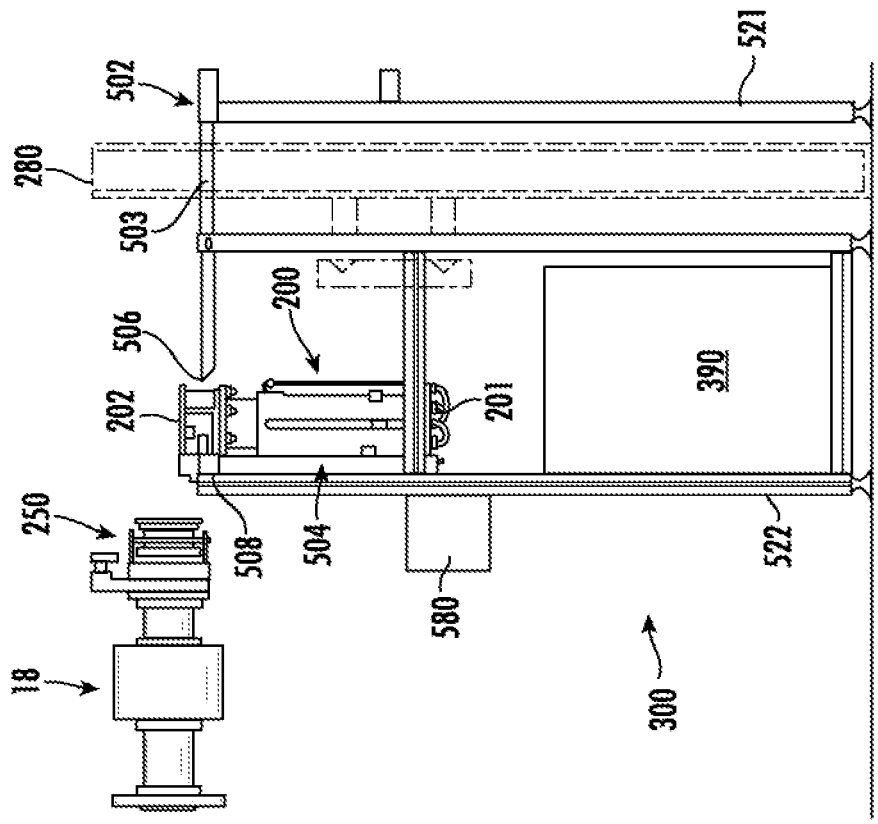
FIG. 5G is a side view of an example embodiment of the target exchange system.
Figure 5F:
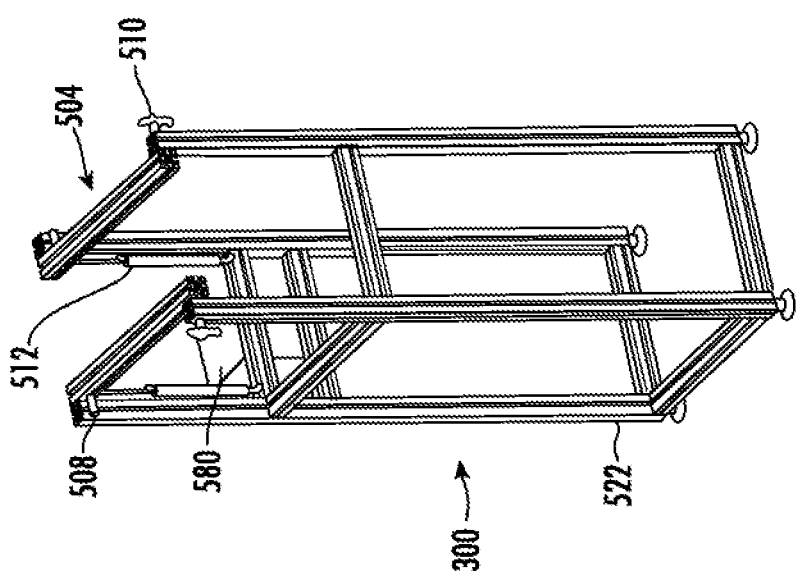
FIG. 5F is a perspective view of an upstream portion of an example embodiment of the target exchange system.

In the reoriented position depicted in FIG. 5G, downstream end 202 of assembly 200 is closest to container 390. If assembly 200 is locked in position in track 505, then the locks can be disengaged and assembly 200 can be lowered into container 390 with downstream and 201 entering first, and thereby quickly placing the most radioactive portion of assembly 200 within the deepest location of shielded container 390. The lowering of assembly 200 can be assisted with a manual or automatic lowering mechanism 580, which in this embodiment is configured as an electrically powered winch. A cable and pulley mechanism (not shown) of winch 580 can be coupled with upstream end 201 of assembly 200 and used to lower assembly 200 into container 390. Alternatively, assembly 200 can be manually lowered into container 390. In some embodiments a disengagable hard stop is present on guide member 504 to prevent assembly 200 from falling into container 390 while being lowered. Once positioned in container 390, assembly 200 can be disconnected from any lowering mechanism and container 390 can be sealed to prevent further exposure to nearby personnel.

Figure 5H:
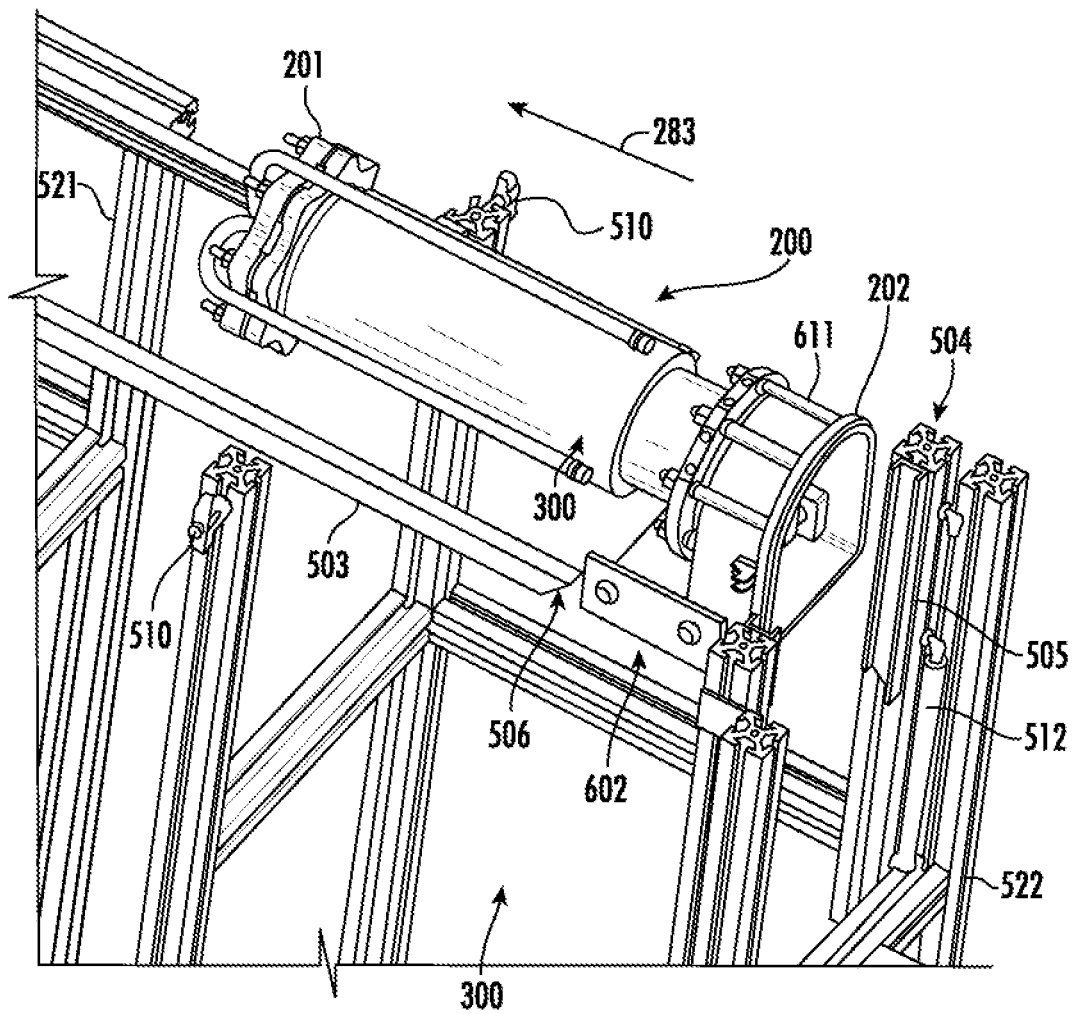
FIG. 5H is a perspective view depicting an example embodiment of the target exchange system during loading of a replacement target assembly.

FIG. 5H is a perspective view depicting the loading of a new target assembly 200 into target exchange system 300. With guide sections 504 in their pivoted position decoupled from track 503, new target assembly 200 can be positioned as shown, either manually or with the assistance of a hoist or other lifting and/or loading mechanism. Carriage 602 can be aligned with interface 506 and inserted into track 503 in upstream direction 283. Guide sections 504 can then be pivoted back into position and locked into place with lock mechanisms 510. The exchange process can then be repeated in reverse to insert new target assembly 200 into BSA 270 and reassemble HEBL 18.

Figure 6A:
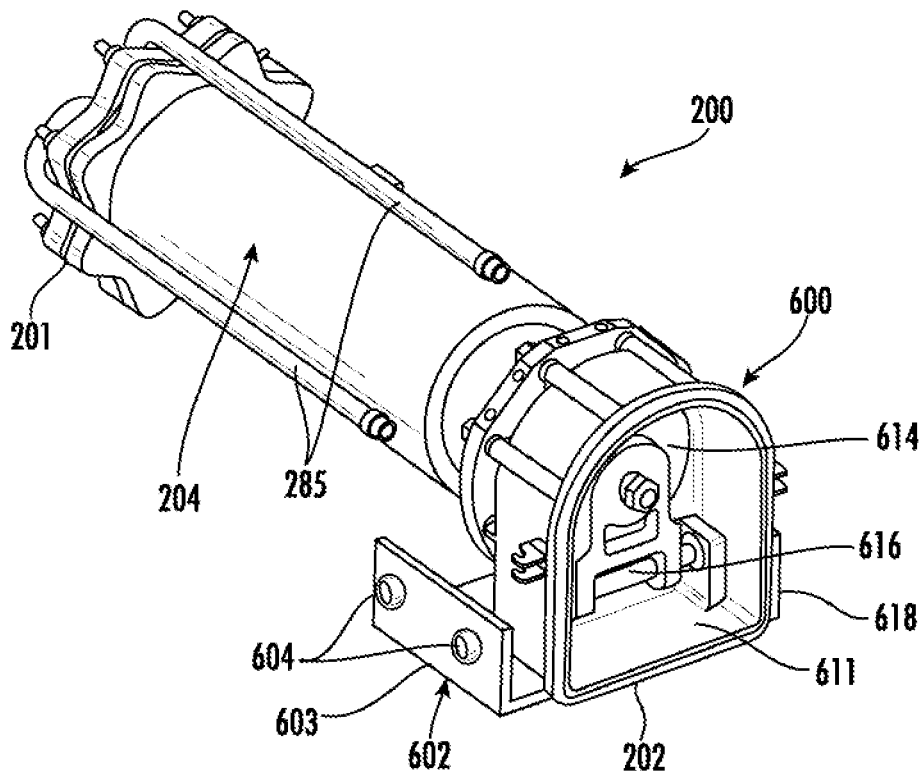
FIG. 6A is a perspective view of an example embodiment of a target assembly.

FIG. 6A is a perspective view depicting an example embodiment of target assembly 200. Here, assembly 200 includes a hollow main body 204. Target device 196 (not shown) is located within downstream end 201, which receives and outputs coolant by way of lines 285. Carriage 602 is coupled with main body 204 at upstream end 201. Carriage 602 can be configured in any manner that permits assembly 202 interface with the guide structure. In this embodiment, carriage 602 includes a frame 603 having wheels 604 rotatably coupled thereto. Wheels 604 are sized to rotate within tracks 503 and 505. Downstream housing 611 of valve 600 is also present at downstream end 202. Valve 600 includes a pivoting seal 614 coupled with a hinge 616. Seal 614 is shown here in the closed position. An actuator 618 can be used to move seal 614 from this closed position to an open position.

Figure 6B:
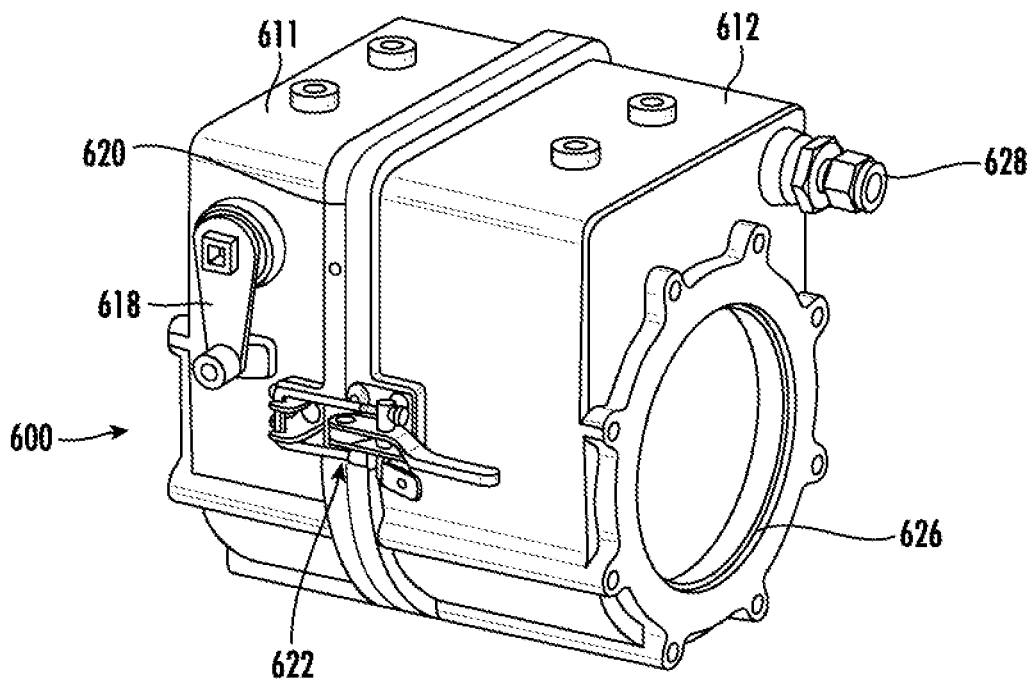
FIG. 6B is an exterior perspective view of an example embodiment of a valve assembly.
Figure 6C:
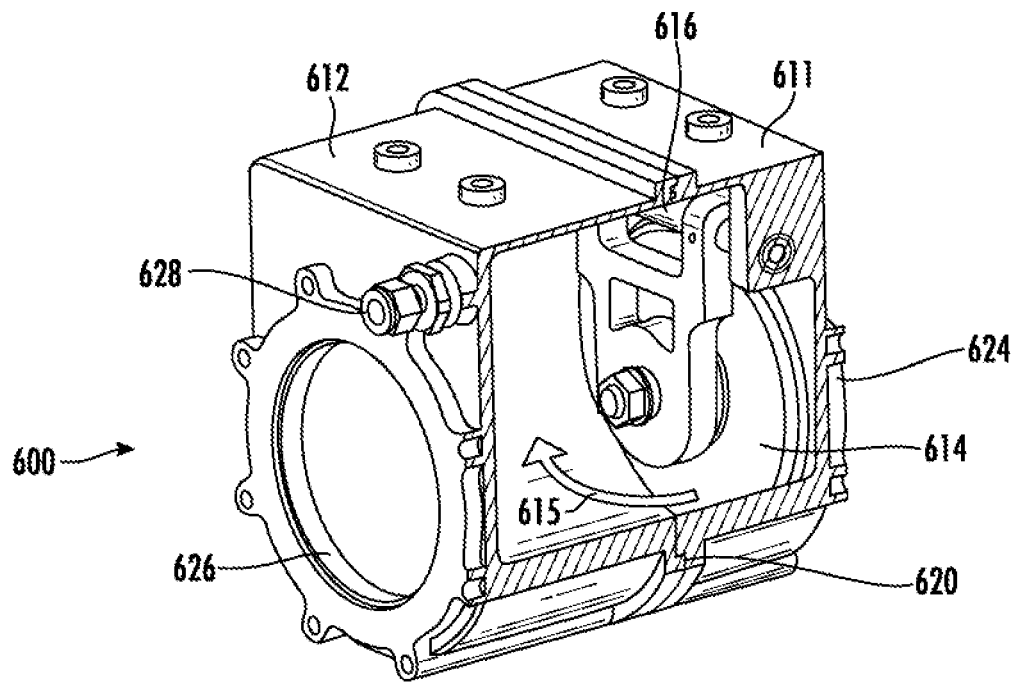
FIG. 6C is an exterior perspective view with a side cutaway of an example embodiment of a valve assembly.
Figure 6D:
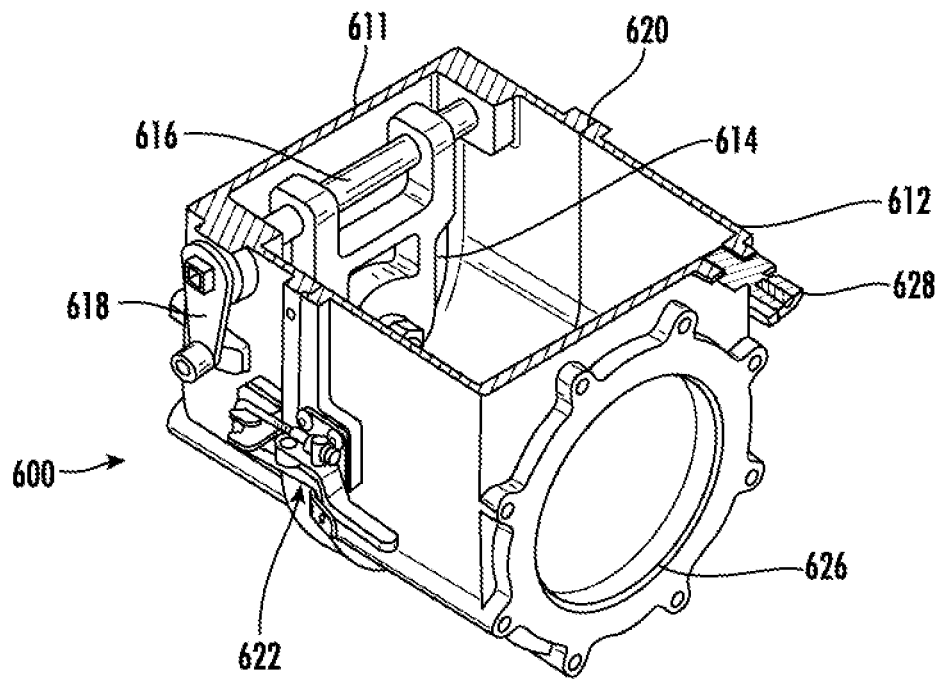
FIG. 6D is an exterior perspective view with a side cutaway of an example embodiment of a valve assembly.

Aspects of this example embodiment of valve 600, with both housing 611 and 612, are now described with reference to FIGS. 6B-6D. FIG. 6B is a perspective exterior view, FIG. 6C is a perspective exterior view with a side cutaway, and FIG. 6D is a perspective exterior view with a top cutaway of valve 600. In this embodiment, actuator 618 is shown as being a manual actuator (e.g., a rotatable crank) but in other embodiments can be an automatic (e.g., electrically powered) actuator. Rotation of actuator 618 causes seal 614 to move in direction 615 (FIG. 6C) from the closed position to an open position. The use of a seal 614 that pivots or rotates between closed and open positions allows the overall size of valve 600 to be minimized thus permitting its movement through aperture 281 of radiation shields 280 without requiring shields 280 to be opened.

Housings 611 and 612 have complementary edge profiles and join together with a gas impermeable seal at interface 620. Housings 611 and 612 are locked together by way of one or more releasable lock mechanisms 622, which in this embodiment is configured as a pull clamp. A similar lock mechanism 622 can be located on the opposite side of valve 600. Lock mechanism 622 is preferably a quick release mechanism to permit rapid disassembly of line section 260 in the presence of potential radioactivity. Examples of quick release lock mechanisms are those that, if manual, require no more than one, no more than two, or no more than three independent actions to unlock the discrete mechanism 622, e.g., a mechanism releasable by a pull, push, and/or turn as opposed to mechanisms that are not readily releasable like a nut and bolt. Automated lock mechanisms can involve more complex sequences of motions to unlock as such can be accomplished quickly given the automated nature or can be accomplished without the presence of human personnel. Other types of lock mechanisms can also be used. After closure of valve 600, actuation of the releasable lock mechanism 622 permits housing 612 to be detached from housing 611 as described with respect to FIGS. 4B and 5C-5E herein.

Housing 611 has an interface 624 for forming a gas impermeable seal with target assembly body 204. Similarly, housing 612 has an interface 626 for forming a gas impermeable seal with line section 260. The gas impermeable seals can be formed with an O-ring (not shown) or other similar elastic sealing member. Valve 600 also includes an access port 628 for, e.g., pressurization and depressurization of the valve interior space.

While valve 600 is described herein as having two housings or portion 611 and 612, the valve mechanism itself is contained within housing 611 and, thus that mechanism can be referred to as the valve with housings 611 and 612 been referred to as segments of the beamline.

As noted above, a target assembly 200 is expected to become radioactive after use; emitting gamma rays through nuclear decay processes having varying half-life characteristics. While the radioactivity of an exhausted target assembly 200 decays, each irradiated target assembly 200 can be stored in the shielded container 390 until the observed level of radioactivity reaches a manageable or acceptable level (e.g., no greater than 1.25 microsievert per hour ($\mu$Sv/hr)). Once the level of radioactivity reaches an acceptable level, the target assembly 200 can be disassembled, the used target device 196 removed, and a replacement target device 196 reassembled into the target assembly 200. This disassembly and reassembly of the target assembly can be performed under a vacuum environment or under an inert gas environment to minimize the potential for undesired reaction of lithium or other compositions that are highly reactive within an atmospheric environment.

Figure 7:
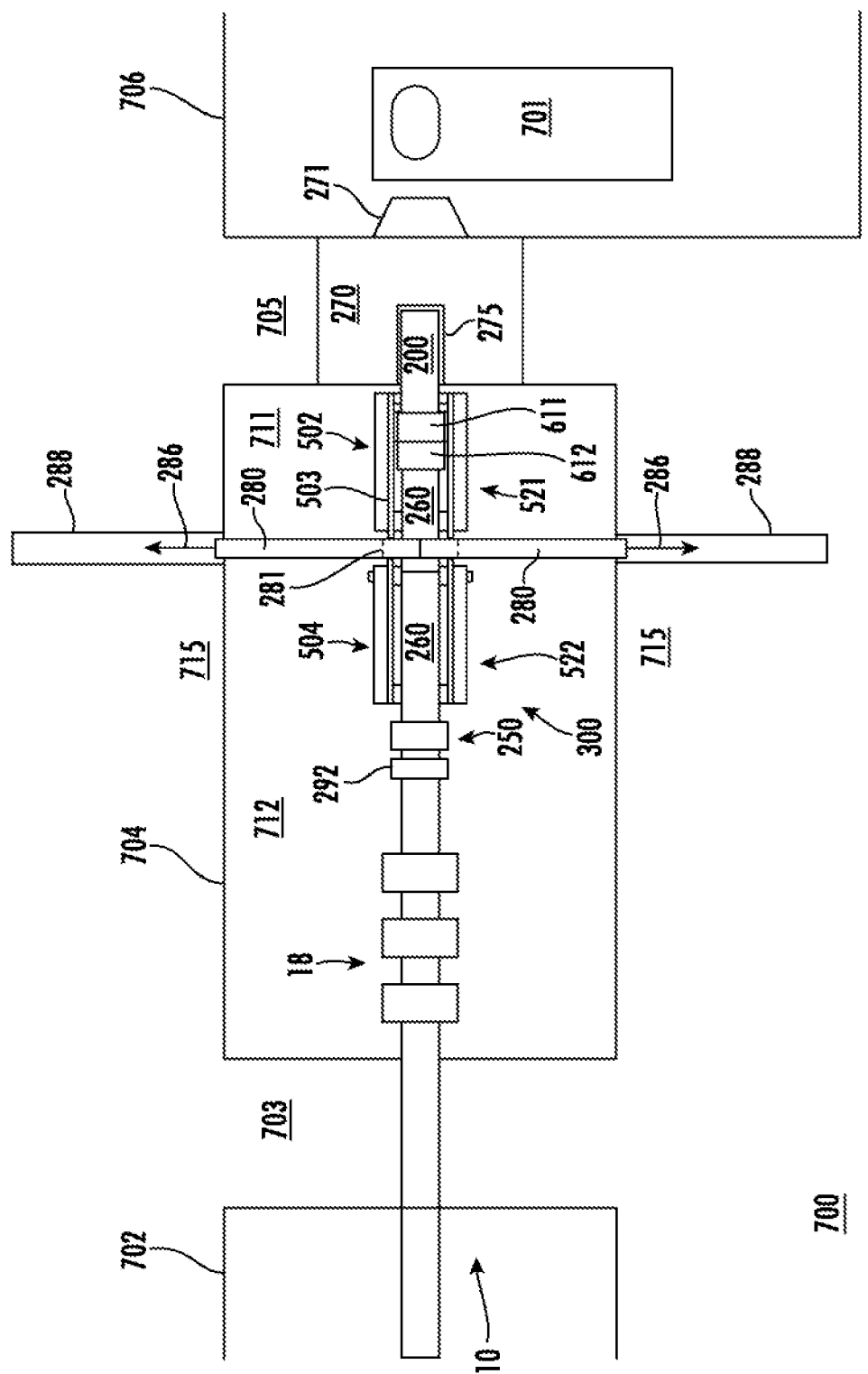
FIG. 7 is a top-down plan view of a portion of a BNCT facility with an example embodiment of a neutron beam system and target exchange system housed therein.

FIG. 7 is a top-down plan view of a portion of a BNCT facility 700 with an example embodiment of a neutron beam system 10 and target exchange system 300 housed therein. Facility 700 includes a first room 702 in which various aspects of neutron beam system 10, such as source 12, LEBL 14, and accelerator 16 (not shown) can be housed. A first wall 703 separates room 702 from a second room 704 in which elements of HEBL 18 and target exchange system 300 are housed. In the configuration shown here, radiation shield doors 280 in their closed position forming aperture 281 around beamline 50. Radiation shield doors 280 can be retracted along, e.g., a roller track (not shown), in the direction of arrows 286 into door housing spaces 288 within facility walls 715. When in the closed position doors 280 divide room 704 into a downstream space 711 and an upstream space 712, which can experience higher levels of radioactivity due to the presence of target assembly 200 therein. The division of target exchange system 300 such that downstream portion 521 is present within space 711 while upstream portion 522 is isolated in space 712 by doors 280 permits much of the target exchange procedure to be accomplished by personnel within space 712, thus protecting them from higher radioactive exposure.

Target assembly 200 is partially present within space 711 and inserted into a cavity 275 within beam shaping assembly 270. A facility wall 705 separates room 704 from a patient treatment room 706, which contains BSA output 271 directed towards a patient support apparatus 701, which in this example is in the form of a bed or table.

The embodiments of target exchange system 300 thus allow the target assembly to be moved directly from the operative position within the BSA 270 to a position within a shielded container 390, for example, in smooth sequence of motions. A new target assembly can be introduced to track section 308 and the sequence of motions can be performed in reverse to install a new target assembly 200 into BSA 270. The compact arrangement of system 300 permits storage with minimal disruption or disassembly of system 10, thus minimizing system downtime. For example, the target assembly 200 can be removed and a new assembly 200 installed without removing or adjusting the portion of any beam optics (e.g., a steering magnet) on HEBL 16. This further minimizes the need to recalibrate beam system 10 after a new target assembly 200 is installed.

Example Shielded Container

Figure 8:
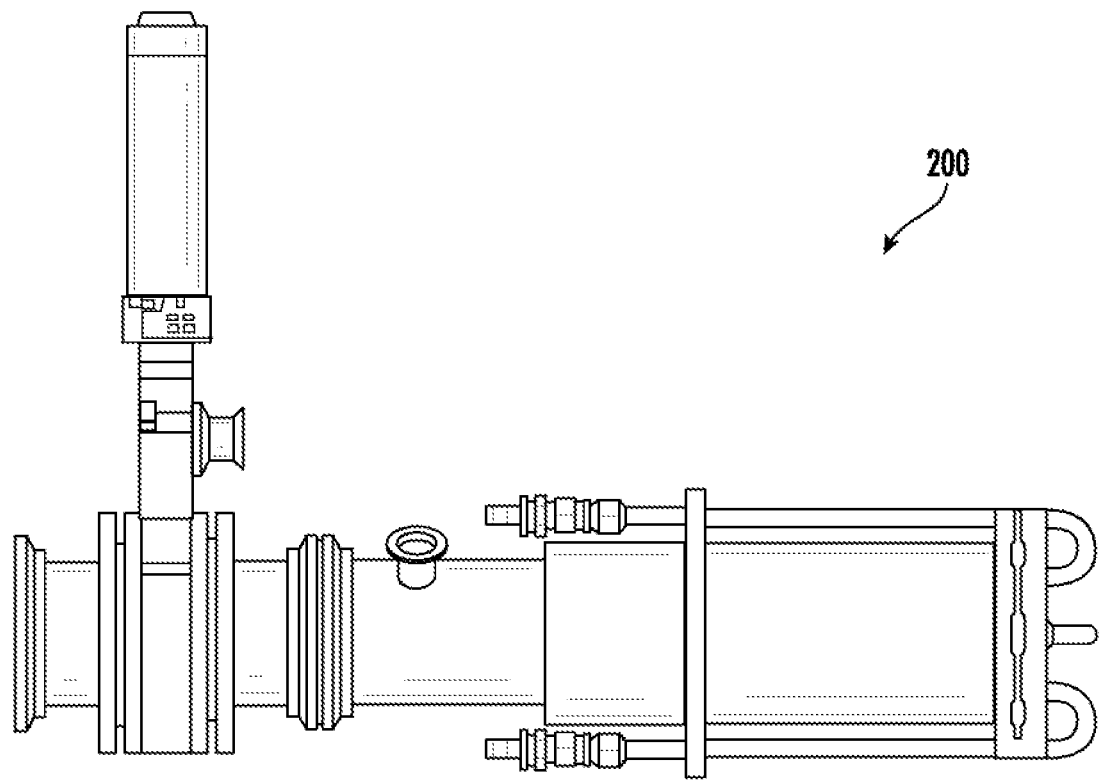
FIG. 8 is a side view of an example embodiment of a target assembly.

To simultaneously satisfy safety and facility demands of minimizing exposure risks to personnel while maintaining a sufficiently useable storage container configuration to facilitate use, various embodiments provide a multi-shell shielded container 390 that enables outer shells to be removed and reused as the level of radioactivity of a target assembly 200 (an example of which is shown in FIG. 8) housed within an innermost shell diminishes. In certain embodiments, one or more of the shells have a variable wall thickness to provide sufficient shielding to a target assembly 200 having a unique radioactivity intensity profile, spatial distribution, and time dependency in gamma emissions while simultaneously minimizing the storage container volume to meet allotted space requirements within a facility.

The walls of each of the one or more shells are configured to block gamma radiation emissions emitted from the target assembly from escaping from the storage container configuration. Thus, the walls of each of the one or more shells include at least one gamma shielding material, such as bismuth, iron, nickel, lead, depleted uranium, aluminum, or copper. Each wall of the one or more shells can be an at least substantially single-material construction (e.g., solid lead). In other embodiments, each wall can be a multi-layer structure, such as having layers of aluminum, copper, and lead (e.g., a single layer of each of multiple materials or multiple layers of each of multiple materials).

In general, tools used to handle radioactive material are very specific to the facility and the metrology of the radioactive material being handled. Moreover, the time dependency and variable intensity of the radiation field has a drastic effect on the amount of shielding required over time.

Figure 9A:
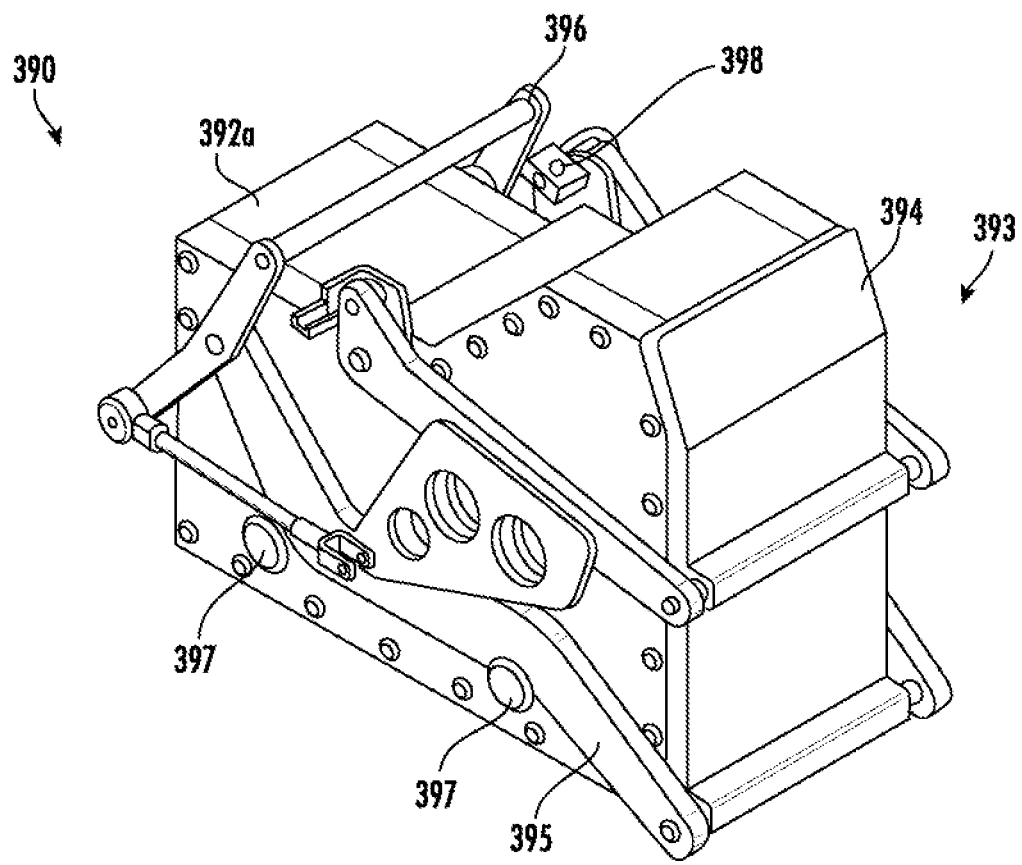
FIG. 9A is a perspective view of an example embodiment of a shielded container configured for manual operation.
Figure 11:
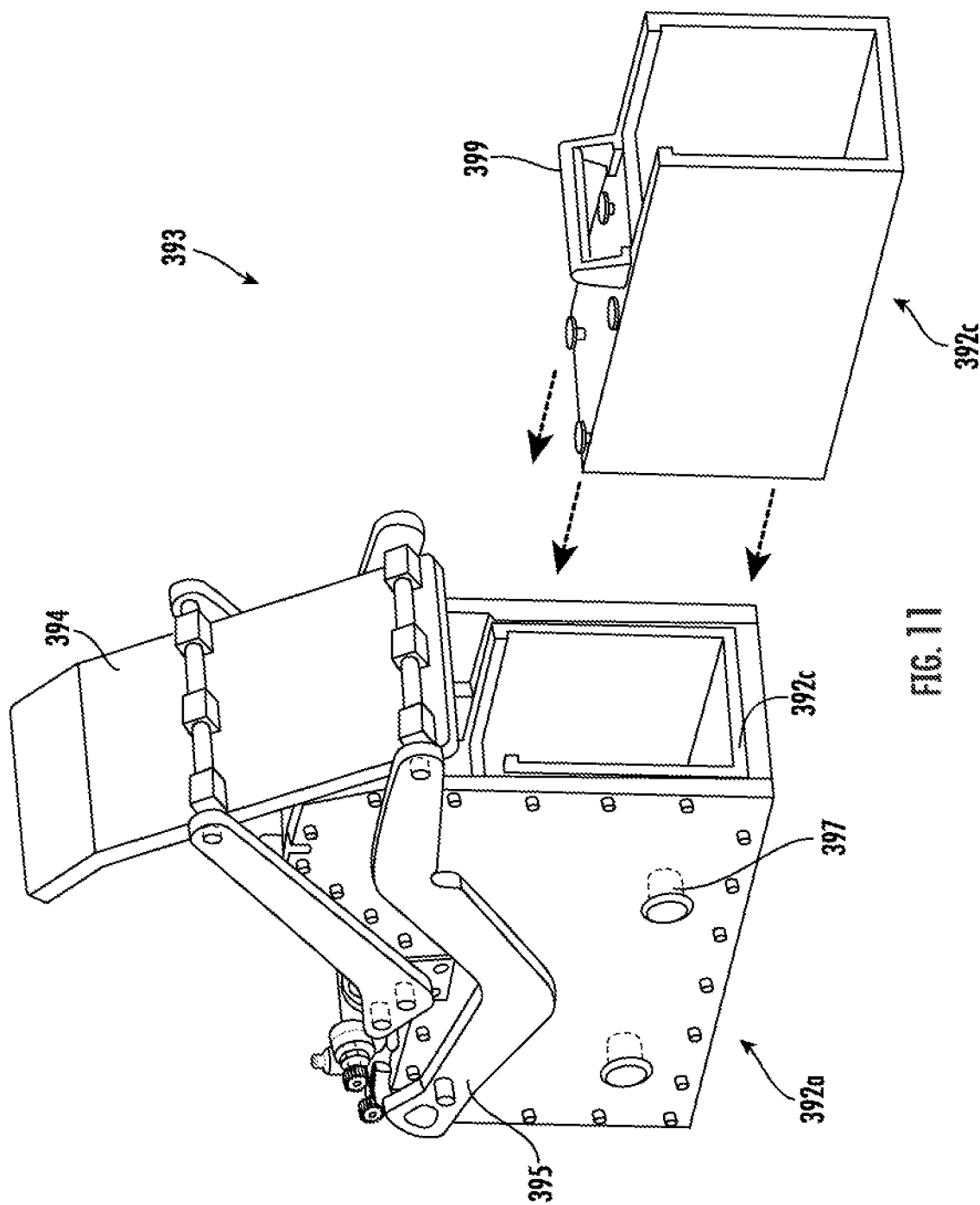
FIG. 11 is a perspective view of an inner shell to be inserted into an outer shell of a shielded container.

FIG. 9A illustrates an example shielded container 390 in accordance with one embodiment. The shielded container 390 illustrated in FIG. A includes multiple container shells 392a-c to address the time dependent decrease in radioactivity (and thus the time-dependent decrease in required shielding of a radioactive target assembly 200), each container shell is embodied as multiple lead shell walls to enclose the discarded target assembly 200 and any included container shells. In certain example embodiments, the shielded container 390 can include three container shells 392a-c, including an outermost shell 392a for use in short-term storage, an interim shell 392b for use in interim storage, and an innermost shell 392c that can be utilized for permanent storage and/or shipping of a discarded target assembly 200. The outer container shell 392a can include multiple outer container shell walls (e.g., and having a respective door), the interim container shell 392b can include multiple interim container shell walls, and the inner container shell 392c can include multiple inner container shell walls. The multiple container shells 392a-c can be configured to nest within one another (e.g., FIG. 9A showing the outermost shell 392a and FIG. 11 illustrating a two-shell configuration showing insertion of the innermost container shell 392c into the outer container shell 392a), such that, when the container shells 392a-c are nested within one another, the shell walls can provide additive shielding protection due to the combined wall thickness of all of the multiple container shells 392a-c. Thus, as the level of radioactive decay decreases over time, the outermost shell 392a can be removed, thereby decreasing the additive thickness of lead shielding while maintaining adequate shielding to protect against radioactive leakage from the container 390.

Figure 10:
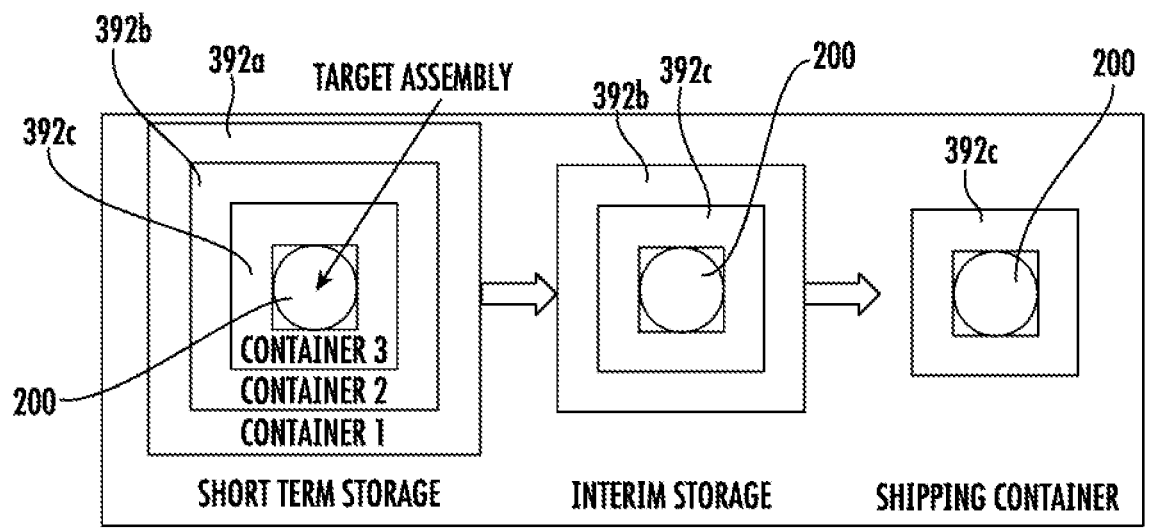
FIG. 10 is a schematic view of an example embodiment of a series of container shells of a shielded container.

With reference to FIG. 9A, within the illustrated example outer container shell 392a (shown in a closed configuration in FIG. 9A and an open configuration in FIG. 11) is a system of one or more nested smaller container shells. Each smaller container shell, in combination with the one or more container shells located within the container shell, can correspond to an amount of shielding desired for a specific duration of time. This is shown conceptually in FIG. 10 with an example shielding container including multiple (e.g., three) container shells 392a, 392b, and 392c. FIG. 11 additionally illustrates a perspective view of insertion of an innermost container shell 392c into an outer container shell 392a of a two-shell configuration (note the innermost container shell 392c is illustrated positioned within the outer container shell 392a and the innermost container shell 392c is also illustrated outside of the outer container shell 392a for purposes of discussion). When the target assembly 200 has been removed from the accelerator, it can be placed in the innermost container shell 392c, which resides inside the interim storage container shell 392b and the outermost, short term storage container shell 392a to provide the maximum shielding thickness due to the use of all three container shells (e.g., thereby providing three layers of container shell thickness), while the target assembly 200 is at its most radioactive point in time.

As the target assembly 200 undergoes radioactive decay, the dose rate decreases and thus the target assembly 200 can be moved to a less shielded configuration (e.g., in the interim storage configuration illustrated in FIG. 10 in which the target assembly 200 remains in the inner most shell 392c, and the innermost shell remains in the interim shell 392b, but the outermost shell 392a is removed), thereby enabling the outermost storage shell 392a to be utilized for another target assembly 200. Subsequently, when the target assembly 200 is adequately decayed, the innermost container shell 392c (e.g., which can be specifically configured for shipping, in certain embodiments) is removed from the interim storage container shell 392b, thereby enabling the interim storage container shell 392b to be available for storage of another target assembly 200.

In summary, the target assembly 200 is stored within the inner container shell 392c, the interim container shell 392b, and the outer container shell 392c for a first period of time immediately after disposing the target assembly 200 within the container 390 while radioactivity of the target assembly is at its highest. The outer container shell 392a can then be removed, and the target assembly 200 can be stored within the inner container shell 392c and the interim container shell 392b for a second period of time immediately after the first period of time during which radioactivity of the target assembly is at a moderate level. The interim container shell 392b can then be removed, and the target assembly 200 can be stored within the inner container shell 392c during a third period of time immediately after the second period of time during which radioactivity of the target assembly is at a low level. Accordingly, during the second period of time and the third period of time, the outer container shell 392a can be repurposed for storage of a different target assembly. Likewise, during the third period of time, the interim container shell 392b can be repurposed for storage of a different target assembly.

Figure 12:
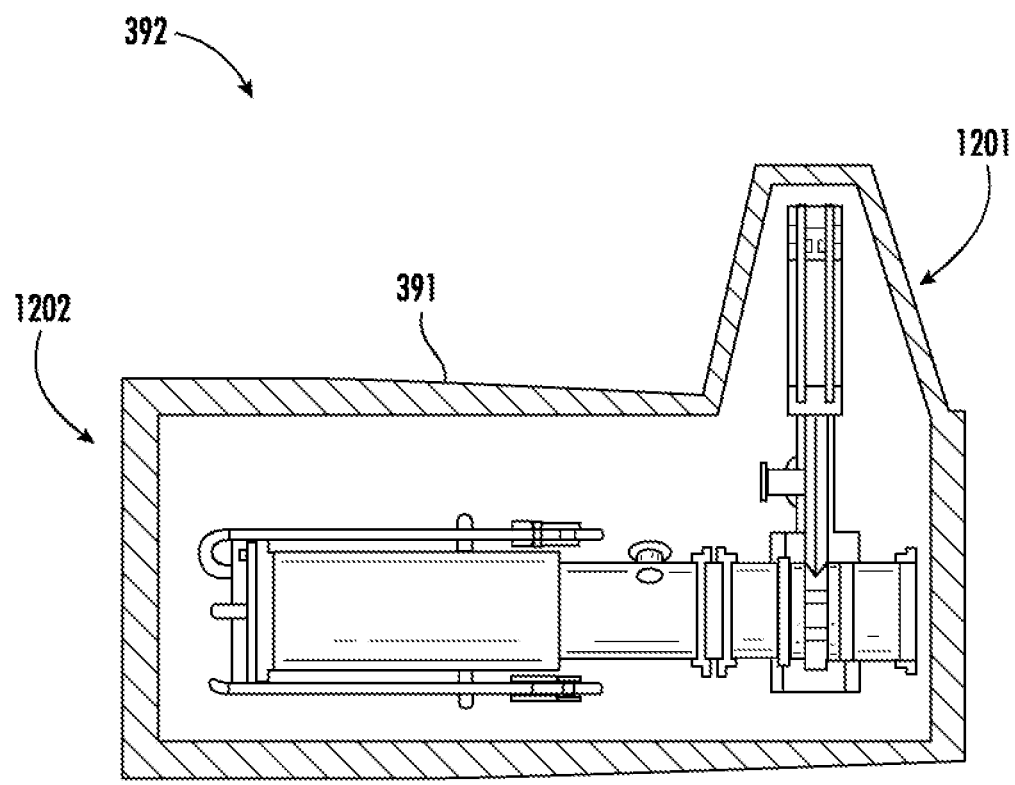
FIG. 12 is a side cutaway view of an example embodiment of a shielded container enclosing a target assembly.

Moreover, each storage container shell can be designed according to the radiation intensity and spatial distribution of the target assembly 200, as reflected in FIGS. 9A-9B. Accordingly, the walls of each storage container shell can vary in thickness to address more or less intense areas of radioactivity of the target assembly 200. An example of a storage container shell having a varying wall thickness is shown in FIG. 12.

In example embodiments, the shielded container 390 can include multiple lead walls and a door assembly including a door 394 (e.g., a shielded, lead-based door) to enable selective access to the interior of the shielded container 390 when placing a target assembly 200 into the shielded container 390 and/or when removing one or more inner container shells 392b-c. In the example embodiment depicted in FIG. 9A, the example outermost shell 392a includes multiple lead shell walls that collectively define an enclosure having an open end 393. The outermost shell 392a additionally includes a door assembly including a door 394 located at the open end 393 and moveable between a closed configuration (e.g., as shown in FIG. 9A) and an open configuration enabling access to an interior of the container shell 392a. In various embodiments, the door assembly includes a mechanical linkage 395 (e.g., a two-bar linkage, a three-bar linkage, a four-bar linkage, a five-bar linkage, and/or the like) configured to move the door 394 relative to the enclosure 392 to ensure the door 394 maintains appropriate alignment with the open end 393 even without careful focus of a user. In various embodiments, the door 394 can maintain an at least substantially parallel orientation relative to the opening 393 during movement between the open configuration and the closed configuration, and between the closed configuration and the open configuration. Thus, the door 394 can be quickly and easily moved between the closed configuration and the open configuration (and vice versa) by a user, by a robot, or by any other source of appropriate mechanical force.

In example embodiments, the mechanical linkage 395 includes multiple (e.g., two) bars secured (e.g., pivotably secured) to the door 394 at respective ends of the multiple bars. The opposite ends of the bars can be secured at pivot points secured relative to the enclosure 392. The multiple bars can be additionally pivotably secured relative to one another (e.g., via one or more cross-member bars), and can be pivotably secured relative to a handle member 396. The handle member extends across a width of the enclosure 392, so as to be easily manipulated by a source of force (e.g., a user's foot, a user's hand, a robot, a solenoid, and/or the like) between a first position (e.g., corresponding to a closed position of the door 394 and as shown for example in FIG. 9A) and a second position (e.g., corresponding to an open position of the door 394, as shown in FIG. 11). The mechanical linkage can be configured to convert the rotational movement of the handle 396 about a pivot point between the first position and the second position into at least substantially linear movement of the door 394. In other embodiments, the mechanical linkage can be configured to translate the rotational movement of the handle about a corresponding pivot point between the first position and the second position to rotational movement of the door 394 relative to the enclosure 392 while maintaining a parallel relationship between the door 394 and the open end 393 of the enclosure to facilitate movement of the door 394 between the open configuration and the closed configuration.

In certain embodiments, the container shell 392a can additionally define one or more bar-stops 397 that, together with edge surrounding the open end 393, serve to support the door 394 and the mechanical linkage 395 in the closed configuration. Moreover, in certain embodiments the container shell 392a can define one or more locking mechanisms 398 that can be movable between a locked configuration and an unlocked configuration for one or more of the open configuration of the container shell 392a and/or the closed configuration of the container shell 392a. Thus, for example, after placing a target assembly 200 into the container 390, the container can be closed, and placed into a locked configuration to prevent unintentional opening of the container while the radioactivity of the target assembly continues to decay.

In certain embodiments, the mechanical linkage 395 and/or the door 394 can be operationally connected with a mechanical linkage and/or a door of a smaller container shell located within the container shell 392a. This operational connection between nested container shells enables multiple nested container shells to be opened or closed with a single actuation (e.g., of handle 396), thereby enabling a target assembly 200 to be placed within an innermost container shell of multiple nested container shells without requiring individual actuation of doors of each nested container shell. In other embodiments, one container (e.g., an outermost container shell or an innermost container shell) can be independently openable, and the remaining containers can be mechanically linked to enable the remaining containers to be opened or closed with a single actuation. Moreover, the operational connection between nested container shells can be selectably engaged and/or disengaged via a corresponding mechanism accessible via an outermost container shell 392a. The selectable engagement and/or disengagement between door assemblies of nested container shells 392a-c can be utilized to disengage the operational connection between door assemblies of nested container shells, for example, when removing a nested container shell 392b-c from an outermost container shell 392a without exposing the contained radioactive target assembly 200.

It will be appreciated that, in certain embodiments, each container shell 392a-c can be independently operable between respective open and closed configurations. Container shells 392a-c nested within other container shells 392a-c can be operable between respective open configuration and closed configurations while placed within containing container shells 392a-c (e.g., and the containing container shells are in an open configuration). In other embodiments, container shells 392a-c can be operable between open configurations and closed configurations when removed from any containing container shells 392a-c.

FIGS. 9B-9C illustrate a shielded container 390 having a configuration similar to that of FIG. 9A, except the mechanical linkage is configured for actuation by an external driving mechanism. As shown specifically in the close-up view of FIG. 9C, the outer container shell 392a includes a drive key 401 configured to be inserted into a drive mechanism (e.g., a rotational motor, a separate linkage for translating rotational movement provided by the user at a safe distance away from the target assembly 200 into rotational movement at the shielded container 390). It should be understood that a drive mechanism is configured for insertion into a drive key 401 having a female configuration. The drive key 401 is mechanically connected with the mechanical linkage 395 via a gearing relationship, such that rotation of the drive key 401 causes movement of the mechanical linkage 395 to open or close the door assembly of the shielded container 390. Under such a configuration, a user need not closely interact with the shielded container 390 during insertion of a radioactive target assembly 200 therein, and can instead rely on mechanized systems for closing and/or opening the door assembly of the shielded container 390 while remaining a safe distance away from the radioactive target assembly 200.

FIG. 11 illustrates one example for insertion of an innermost container shell 392c into an outer container shell 392a in a two-shell embodiment. It should be understood that analogous processes can be utilized for insertion of an interim container shell 392b in a three-shell configuration (e.g., and for insertion of an innermost container shell 392c into an interim container shell 392b in a three-shell configuration). As shown in FIG. 11, the innermost container shell 392c defines an outside surface configured to slide into an interior of the outer container shell 392a. In the illustrated embodiment, the outer surface of the innermost container shell 392c is generally smooth, so as to enable the innermost container shell 392c to slide easily into the outer container shell 392a. However, it should be understood that in certain embodiments, the outer surface of the innermost container shell 392c can define one or more alignment features, such as rails, tracks, and/or other alignment features that mate with and engage corresponding alignment features of an interior surface of the outer container shell 392a to facilitate alignment and sliding of the innermost container shell 392c into the interior of the outer container shell 392a. Moreover, although not shown, one of the outer surface of the innermost container shell 392c or the interior surface of the outer container shell 392a can include one or more bearings (e.g., ball bearings, sliding surfaces, and/or the like) to decrease frictional forces between the outer container shell 392a and the innermost container shell 392c.

Moreover, as shown in FIG. 11, the innermost container shell 392c defines an opening on an end of the innermost container shell 392c configured to accept a target assembly 200 therein. As shown, the opening of the innermost container shell 392c can be provided such that portions of the target assembly 200 predicted to have a lower level of radioactivity are located outside of the innermost container shell 392c, and such that shielding of these portions is provided specifically by the outer container shell 392a (and/or interim container shell 392b in a three-shell configuration). As mentioned herein, the innermost container shell 392c is defined by shielding walls, such as lead-based walls, although other shielding materials and/or layer structures can be utilized as discussed herein. As additionally reflected in FIG. 11, the innermost container shell 392c can define a handle 399 to facilitate insertion and removal of the innermost container shell 392c into and out of the outer container shell 392a (or the interim container shell 392b). The handle 399 can additionally serve to ensure proper positioning of the innermost container shell 392c within the outer container shell 392a, such as by stopping movement of the innermost container shell 392c when the handle 399 contacts a surface within the interior of the outer container shell 392a. It should be understood that while the interim container shell 392b is not shown in FIG. 11 (for a three-shell configuration), the interim container shell can have a configuration analogous to that of the innermost container shell 392c, but with an interior sized to accommodate the innermost container shell 392a.

With reference to FIG. 12, the walls of each container shell 392a-c can have a thickness profile specifically configured to provide adequate shielding to the target assembly 200, and more specifically to the radioactivity of individual portions of the target assembly 200. Thus, the thickness profile of any of the container shells 392a-c defines a wall thickness that varies based on a proximity to a target 100 of the target assembly 200, when the target assembly 200 is positioned within the container shell. Specifically, portions of the container shell 392 (whether the outer container shell 392a, the interim container shell 392b, or the inner container shell 392c) has a thicker container shell wall nearer to the target 100 than portions of the container shell located farther from the target 100. Thus, as shown in FIG. 12, the shell walls can have a variable wall thickness, such as between a first shell wall thickness portion 1201 (e.g., having a thin wall thickness to shield areas of a target assembly expected to have relatively low levels of radioactivity) and a second shell wall thickness portion 1202 (e.g., having a thick wall thickness to shield areas of a target assembly expected to have relatively high levels of radioactivity). The thickness of the shell wall (specifically, the thickness of each portion of the shell wall, such as the first shell wall thickness portion 1201 and the second shell wall thickness portion 1202) is tailored to the location of the radioactive target 100 within the target assembly 200, such that portions of the shell wall that are proximate to the radioactive target 100 are thicker than portions of the shell wall that are farther away from the radioactive target 100 when the target assembly is housed within the container shell 392 to provide additional shielding against radiation from the radioactive target 100. In the illustrated example of FIG. 12, the first shell wall thickness portion 1201 is thinner than the second shell wall thickness portion 1202 because the second shell wall thickness portion 1202 is proximate the expected location of the radioactive target 100 when the target assembly is housed within the container shell 392. In an example, the second shell wall thickness portion 1202 is at least twice as thick as the first shell wall thickness portion 1201.

The container shell 392 illustrated in FIG. 12 is shaped to accommodate the target assembly 200 shown in FIG. 12, and the container shell 392 of FIG. 12 has wall thickness portions to address the expected radiation levels from various portions of the target assembly 200 (e.g., as mentioned, the first shell wall thickness portion 1202 is thicker than the second shell wall thickness portion 1201 due to the expected location of the radioactive target 100 when the target assembly 200 is positioned within the container shell 392. However, the container shell 392 can have other shapes and wall thickness configurations to accommodate other target assembly configurations, such as to accommodate a target assembly 200 as shown in FIG. 6A with an included compact valve assembly 600.

It will be appreciated that the thicknesses illustrated in FIG. 12 are merely examples, and any of a variety of thickness profiles can be provided, with different thickness values and different levels of thickness variability between a thinnest portion of a container shell wall 391 and a thickest portion of a container shell wall 391. Moreover, it will be appreciated that each of the multiple nested container shells can be characterized by differences in thickness profiles. For example, as the level of radioactivity of the target device decays, the difference in radioactivity between a least-radioactive portion of the target device and the most-radioactive portion of the target device will decrease (e.g., as radioactive decay typically occurs according to an exponential decay curve), and therefore, and innermost container shell 392c to be utilized alone when the target device 200 has sufficiently decayed to minimize safety concerns, can be characterized by a wall thickness profile having a minimal level of difference between a thickest-portion wall 391 and a thinnest-portion wall 391.

By contrast, the outermost shielding container shell 392a, utilized to aid in containment of radioactivity of a target assembly while the target assembly is most-radioactive, is characterized by a largest difference in thickness between a thickest portion of a container wall 391 and a thinnest portion of the container wall 391 of the container shell 392a (thereby addressing the significantly higher levels of radioactivity of certain portions of the target assembly 200). By extension, the interim storage container shell 392b can be characterized by an intermediate difference in wall thickness between a thinnest-portion of a container wall 391 and a thickest-portion of a container wall 391, to reflect the intermediate levels of radioactivity of the target assembly 200 during a second period of time.

Shielded containers 390 as discussed herein, when utilized together with target assembly exchange configurations as discussed herein provide advantages of enabling exchange and storage of target assemblies 200 while minimizing exposure of personnel to any radioactive isotopes expelled from a target assembly 200. Moreover, by providing multiple nested container shells 392a-c, one or more container shells 392a-c can be reused without exposing a contained radioactive target assembly 200 to a surrounding environment, thereby simultaneously providing safety to personnel handling or otherwise working with a target assembly 200 contained within a shielding container 390 and minimizing the amount of shielding material needed to provide adequate shielding to multiple target assemblies 200 (e.g., sequentially exchanged target assemblies 200). Moreover, the mechanical linkage 395 and handle configuration 396 as discussed herein enables mechanical, pneumatic, hydraulic, and/or manual operation of a door assembly, thereby enabling operation of the door assembly at a safe distance away from the shielding container 390.

The shielding container 390, including the multiple shielding container shells 392a-c is mobile, minimal in cross-section, and compact, and can be provided in a configuration specific to a target assembly 200 (or other radioactive device) to be stored therein during radioactive decay. The shielding container 390 (and the individual shielding container shells 392a-c) can be further tailored to the overall shape of the target assembly 200, the unique radiation profile of the target assembly 200, the unique decay time characteristics of the target assembly 200, and/or other facility-specific unique characteristics.

Although the provided example includes three shielding container shells 392a-c, it should be understood that a shielding container 390 can include any number of shielding container shells, such as two shielding container shells, two shielding container shells, five shielding container shells, and/or the like. In certain embodiments, a single shielding container shell can be utilized for storage of certain target assemblies 200.

Example Vacuum-Activated Storage Container

To minimize a risk of subjecting replacement target devices 196 (or other volatile objects) to potentially damaging reactions in an atmospheric environment, the target devices 196 are maintained in vacuum and/or inert environments during manufacture, storage, transportation, installation into a target assembly 200 (an isolated view thereof is shown at FIG. 8), and use. As discussed herein, the target assembly 200 itself is configured to maintain a vacuum environment around the target device 196 even while the target assembly 200 is not installed within the particle accelerator. However, replacement target devices 196 must be transported from a manufacturing location to an installation location where the target devices 196 are exposed to a surrounding environment while the target assembly 200 is opened and the target device 196 is inserted into the target assembly 200. To maintain a vacuum or inert environment surrounding the target device 196 during storage and transportation, a vacuum-activated storage container is provided that securely stores a target device 196 therein while maintaining a vacuum or inert environment therein.

Figure 13:
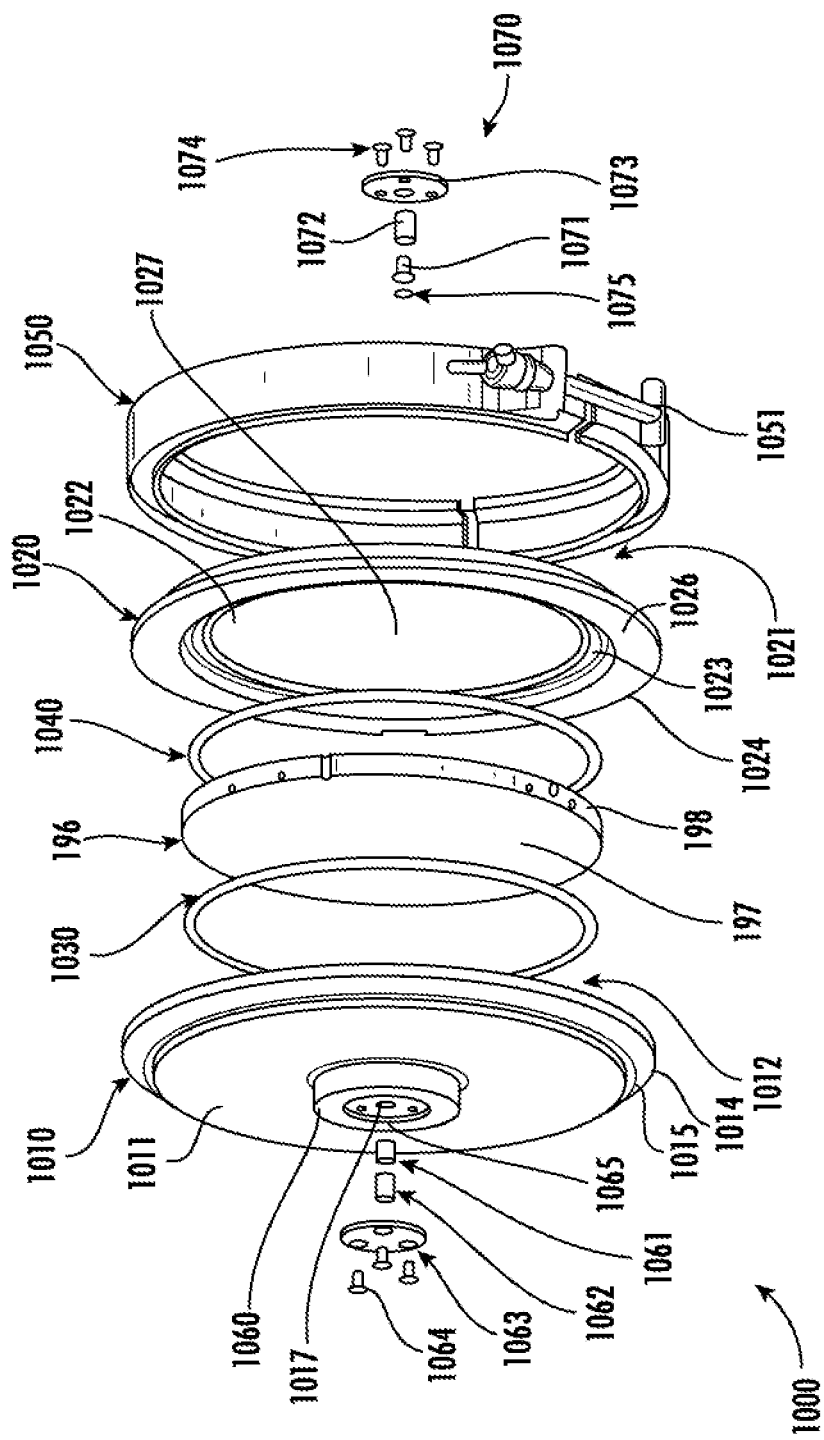
FIG. 13 is an exploded view of a vacuum-actuated storage container enclosing a target device.

FIG. 13 is an exploded view of a vacuum-activated storage container 1000 according to one embodiment. As shown, the illustrated vacuum-activated storage container 1000 is housing a volatile object embodied as a target device 196 shown within an interior thereof. It should be understood that other volatile objects (e.g., disks of solid volatile material, slurries of volatile material, and/or the like) can be stored within a vacuum-activated storage container 1000 according to certain embodiments.

As shown in FIG. 13 and as discussed above, the target device 196 is embodied as a disk (e.g., an at least substantially circular disk) having a first surface 197 and an opposite second surface (not shown), separated by a perimeter edge 198. The disk can include a metallic material, such as copper, although other metal materials can be utilized for various target device 196 configurations. Moreover, the target device 196 can additionally include a volatile composition (e.g., lithium, magnesium, sodium, and/or the like) coated onto the first surface 197 of the disk. The coating can extend to edges of the first surface of the disk, or edges of the coating can be space a distance internal to the edge of the disk, such that a ring of exposed metal material surround the coating on the first surface 197 (in certain embodiments, a holding member, discussed herein, can engage the exposed metal when the target device 196 is positioned within the vacuum-activated storage container 1000 so as not to disturb the coating).

The vacuum-activated storage container 1000 illustrated in FIG. 13 includes a shell case assembly and a coupling device 1050 (embodied as a ring clamp in the illustrated embodiment of FIG. 13). The shell case assembly includes a first shell case side 1010 and a second shell case side 1020. In the illustrated embodiment, the first shell case side 1010 and the second shell case side 1020 have at least substantially identical configurations, however it should be understood that in certain embodiments, various features of the first shell case side 1010 can differ from features of the second shell case side 1020. In certain embodiments, the first shell case side 1010 and the second shell case side 1020 can include aluminum, however other rigid materials that are not subject to gas permeation therethrough can be utilized in other embodiments (e.g., stainless steel, rigid polymers, and/or the like). The construction material, thickness, and overall dimensions of the first shell case side 1010 and the second shell case side 1020 can be selected to impede deformation of the first shell case side 1010 and/or the second shell case side 1020 (e.g., mechanical deformation, such as bending or twisting; thermal deformation such as bending, twisting, expansion, or shrinkage; and/or the like), as deformation of either of the first shell case side 1010 and/or the second shell case side 1020 can include an air-tight seal formed between the first shell case side 1010 and the second shell case side 1020. Moreover, the manufacture of the first shell case side 1010 and the second shell case side 1020 can be performed so as to ensure highly precise surface positions and finishes to mitigate against imperfections within the first shell case side 1010 or the second shell case side 1020 that can include an air-tight seal therebetween. For example, each of the first shell case side 1010 can be machined (e.g., milled) to a tight dimensional tolerance and with highly precise surface finishing to maximize the effectiveness of an air-tight seal formed between the first shell case side 1010 and the second shell case side 1020. However, it should be understood that any of a variety of manufacturing techniques can be utilized, such as stamping, molding, casting, and/or the like.

In the illustrated embodiment of FIG. 13, each of the first shell case side 1010 and the second shell case side 1020 have an at least substantially circular shape. However, it should be understood that other shapes can be usable, with the first shell case side 1010 and the second shell case side 1020 having matching shapes enabling sealing surfaces (e.g., interior surfaces of flanges, as discussed herein) of each of the first shell case side 1010 and the second shell case side 1020 to engage relative to one another so as to form an air-tight seal therebetween.

As shown, the first shell case side 1010 defines an exterior surface 1011 (which is positioned external to the vacuum-activated storage container 1000 when in a closed configuration) and an opposite interior portion. The interior portion is defined by an interior surface 1012 inset relative to a perimeter of the interior portion. The interior portion, when aligned with the interior portion of the second shell case side 1020, forms an enclosed interior volume of the vacuum-activated storage container 1000 within which the volatile object (e.g., target device 196) can be positioned. Moreover, the interior surface 1012 of the illustrated embodiment defines an inset channel (not shown) surrounding the interior surface 1012 adjacent the perimeter of the interior surface 1012. As shown in FIG. 13, a holding member 1030 seats into the inset channel so as to extend proud of the interior surface 1012. The holding member 1030 of the illustrated embodiment includes a resilient material having a coefficient of friction higher than the interior surface 1012. As examples, the holding member 1030 can include a rubber material, a resilient polymer material, and/or the like. The holding member 1030 includes a material that is not reactive with the material of the first shell case side 1010, the metal material of the disk of the target device 196, or the coating composition of the target device 196. In the illustrated embodiment, the holding member 1030 is embodied as an O-ring seated in the inset channel. The holding member 1030 is configured to contact and thereby frictionally engage the first surface 197 of the target device 196 when the vacuum-activated storage container 1000 is in a closed configuration to provide a supportive holding force to the target device 196 to mitigate against potential damage to the target device 196 that can arise from the target device 196 impacting surfaces of the enclosed interior volume during transit of the vacuum-activated storage container 1000.

As shown in FIG. 13, the first shell case side 1010 further defines a flange 1014 extending around a perimeter of the first shell case side 1010. The flange 1014 defines an exterior surface 1015 extending around the exterior surface 1011 of the first shell case side 1010, and an opposite interior surface (not shown) extending around an interior portion of the first shell case side 1010. In the illustrated embodiment, the exterior surface 1015 is offset relative to the exterior surface 1011 of the first shell case side 1010. The offset between the exterior surface 1015 of the flange 1014 and the exterior surface 1011 of the first shell case side 1010 can be dimensioned based on a corresponding dimension of a coupling device 1050, such that the exterior surface 1011 of the first shell case side 1010 is at least substantially planar with an edge of the coupling device 1050 when the coupling device 1050 is secured thereto. Moreover, the exterior surface 1015 of the flange 1014 is chamfered, extending from a thick portion immediately adjacent the exterior surface 1011 of the first shell case side 1010, to a thin portion defining the overall perimeter edge of the first shell case side 1010. The interior surface of the flange 1014 is a smooth, at least substantially planar surface configured to engage an interior surface 1026 of flange 1024 of the second shell case side 1020 to form an air tight seal therebetween. In certain embodiments, one or both of the interior surface of flange 1014 or interior surface 1026 of flange 1026 can have a sealing coating (e.g., a pressure-activated adhesive, a resilient material, and/or the like) to facilitate formation of an airtight seal between the interior surface of flange 1014 and interior surface 1026 of flange 1024.

By providing a chamfer on the exterior surface 1015 of the flange 1014, placing a coupling device 1050 (e.g., a ring clamp) around the perimeter of the first shell case side 1010 and second shell case side 1020 such that the coupling device 1050 engages the exterior surface 1015 of the flange 1014, tightening the coupling device 1050 (e.g., by decreasing a diameter of the ring clamp) creates a force vector compressing the interior surfaces of the flanges 1014, 1024 of the first shell case side 1010 and the second shell case side 1020 against one another to facilitate formation of an air-tight seal therebetween.

As shown in FIG. 13, the first shell case side 1010 includes a vacuum-activated check valve 1060 located at a hole 1017 extending through the first shell case side 1010 from the exterior surface 1011 to the interior surface 1012. The vacuum-activated check valve 1060 includes a piston 1061 movable axially within the hole 1017. Although not visible within FIG. 13, the hole 1017 defines a piston seat, against which a surface of the piston 1061 rests in a sealed configuration to form an airtight seal therebetween. Moreover, the piston seat can additionally include a sealing member 1065 (e.g., an O-ring) against which the surface of the piston 1061 seats when in the sealed configuration. The piston seat can be a chamfered portion to engage an exterior surface of the piston 1061 having a corresponding chamfer. The piston seat can alternatively be a stepped surface within the hole 1017, against which an exterior surface of the piston 1061 engages when in the sealed configuration. It should be understood that other piston seat configurations can be utilized in accordance with various embodiments.

The vacuum-activated check valve additionally includes a spring 1062 that biases the piston to the sealed configuration against the piston seat. In certain embodiments, the spring 1062 can have a compressive force that can be overcome to move the piston 1061 to an open configuration by a difference in environmental pressure of at least 1 mbar between a pressure at an exterior end of the hole 1017 (at the exterior surface 1011) and a pressure at an interior end of the hole 1017 (at the interior surface 1012), where the pressure at the interior end of the hole 1017 is at least 1 mbar higher than the pressure at the exterior end of the hole 1017. Such a spring constant ensures that a vacuum pressure is maintained within an enclosed interior volume of the vacuum-activated storage container 1000, while allowing the interior of the vacuum-activated storage container 1000 to equalize with an environmental pressure outside of the vacuum-activated storage container 1000 when the pressure outside to the vacuum-activated storage container 1000 is lower than a pressure within the enclosed interior of the vacuum-activated storage container 1000. As shown in FIG. 13, the components of the vacuum-activated check valve 1060, including the piston 1061 and spring 1062 are held within the hole 1017 by cap 1063, which is secured to the first shell case side 1010 via fasteners 1064 (e.g., screws).

As noted above, the second shell case side 1020 can have a configuration identical to that of the first shell case side 1010.

Accordingly, the second shell case side 1020 defines an exterior surface 1021 (which is positioned external to the vacuum-activated storage container 1000 when in a closed configuration) and an opposite interior portion. The interior portion is defined by an interior surface 1022 inset relative to a perimeter of the interior portion. The interior portion, when aligned with the interior portion of the first shell case side 1010, forms an enclosed interior volume of the vacuum-activated storage container 1000 within which the volatile object (e.g., target device 196) can be positioned. Moreover, the interior surface 1022 of the illustrated embodiment defines an inset channel 1023 surrounding the interior surface 1022 adjacent the perimeter of the interior surface 1022. As shown in FIG. 13, a holding member 1040 seats into the inset channel 1023 so as to extend proud of the interior surface 1022. The holding member 1040 of the illustrated embodiment includes a resilient material having a coefficient of friction higher than the interior surface 1022. The holding member 1040 can be identical to holding member 1030, discussed above. In the illustrated embodiment, the holding member 1040 is an O-ring seated in the inset channel. The holding member 1040 is configured to contact and thereby frictionally engage the second surface of the target device 196 when the vacuum-activated storage container 1000 is in a closed configuration to provide a supportive holding force to the target device 196 to mitigate against potential damage to the target device 196 that can arise from the target device 196 impacting surfaces of the enclosed interior volume during transit of the vacuum-activated storage container 1000.

As shown in FIG. 13, the second shell case side 1020 further defines a flange 1024 extending around a perimeter of the second shell case side 1020. The flange 1024 defines an exterior surface (not shown) extending around the exterior surface 1021 of the second shell case side 1020, and an opposite interior surface 1026 extending around an interior portion of the second shell case side 1020. In the illustrated embodiment, the exterior surface is offset relative to the exterior surface 1021 of the second shell case side 1020. The offset between the exterior surface of the flange 1024 and the exterior surface 1021 of the second shell case side 1020 can be dimensioned based on a corresponding dimension of a coupling device 1050, such that the exterior surface 1020 of the second shell case side 1020 is at least substantially planar with an edge of the coupling device 1050 when the coupling device 1050 is secured thereto. Moreover, the exterior surface of the flange 1024 is chamfered, extending from a thick portion immediately adjacent the exterior surface 1021 of the second shell case side 1020, to a thin portion defining the overall perimeter edge of the second shell case side 1020. The interior surface 1026 of the flange 1024 is a smooth, at least substantially planar surface configured to engage an interior surface of flange 1014 of the first shell case side 1010 to form an air tight seal therebetween.

By providing a chamfer on the exterior surface of the flange 1024, placing a coupling device 1050 (e.g., a ring clamp) around the perimeter of the first shell case side 1010 and second shell case side 1020 such that the coupling device 1050 engages the exterior surface of the flange 1024, tightening the coupling device 1050 (e.g., by decreasing a diameter of the ring clamp) creates a force vector compressing the interior surfaces of the flanges 1014, 1024 of the first shell case side 1010 and the second shell case side 1020 against one another to facilitate formation of an air-tight seal therebetween.

As shown in FIG. 13, the second shell case side 1020 includes a vacuum-activated check valve 1070 located at a hole 1027 extending through the second shell case side 1020 from the exterior surface 1021 to the interior surface 1022. However, it should be understood that in certain embodiments, the second shell case side 1020 does not have a check valve 1070. The illustrated vacuum-activated check valve 1070 includes a piston 1071 movable axially within the hole 1027. Although not visible within FIG. 13, the hole 1027 defines a piston seat, against which a surface of the piston 1071 rests in a sealed configuration to form an airtight seal therebetween. Moreover, the piston seat can additionally include a sealing member 1075 (e.g., an O-ring) against which the surface of the piston 1071 seats when in the sealed configuration. The piston seat can be a chamfered portion to engage an exterior surface of the piston 1071 having a corresponding chamfer. The piston seat can alternatively be a stepped surface within the hole 1027, against which an exterior surface of the piston 1071 engages when in the sealed configuration. It should be understood that other piston seat configurations can be utilized in accordance with various embodiments.

The vacuum-activated check valve additionally includes a spring 1072 that biases the piston to the sealed configuration against the piston seat. In certain embodiments, the spring 1062 can have a compressive force that can be overcome to move the piston 1071 to an open configuration by a difference in environmental pressure of at least 1 mbar between a pressure at an exterior end of the hole 1027 (at the exterior surface 1021) and a pressure at an interior end of the hole 1027 (at the interior surface 1022), where the pressure at the interior end of the hole 1027 is at least 1 mbar higher than the pressure at the exterior end of the hole 1027. Such a spring constant ensures that a vacuum pressure is maintained within an enclosed interior volume of the vacuum-activated storage container 1000, while allowing the interior of the vacuum-activated storage container 1000 to equalize with an environmental pressure outside of the vacuum-activated storage container 1000 when the pressure outside to the vacuum-activated storage container 1000 is lower than a pressure within the enclosed interior of the vacuum-activated storage container 1000. As shown in FIG. 13, the components of the vacuum-activated check valve 1070, including the piston 1071 and spring 1072 are held within the hole 1027 by cap 1073, which is secured to the first shell case side 1020 via fasteners 1074 (e.g., screws).

Although the illustrated second shell case side 1020 is described as including a vacuum-activated check valve 1070, it should be understood that in certain embodiments, only the first shell case side 1010 includes a vacuum-activated check valve 1060, and the second shell case side 1020 does not define any holes extending therethrough, such that the vacuum-activated check valve 1060 of the first shell case side 1010 is configured to maintain the vacuum pressure within the enclosed interior volume of the vacuum-activated storage container 1000.

Moreover, in the illustrated embodiment of FIG. 13, the first shell case side 1010 is disconnected from the second shell case side 1020 when the vacuum-activated storage container 1000 is in an open configuration. However, in other embodiments, the first shell case side 1010 can remain movably connected with the second shell case side 1020 when in the open configuration, such as via a hinge, a floating hinge, a flexible line extending between the components, and/or the like.

The illustrated embodiment of FIG. 13 additionally includes a coupling device 1050 configured to secure the first shell case side 1010 relative to the second shell case side 1020 when the pressure within the enclosed interior portion is at least substantially equal to the pressure surrounding the vacuum-activated storage container 1000. When a vacuum pressure is formed within the enclosed interior portion of the vacuum-activated storage container 1000 and the pressure inside the enclosed interior portion is lower than the ambient pressure surrounding the vacuum-activated storage container 1000, the ambient pressure surrounding the vacuum-activated storage container 1000 creates a holding force to maintain the first shell case side 1010 and the second shell case side 1020 in a closed and sealed configuration. However, when the pressure within the enclosed interior volume is at least substantially equal to the ambient pressure surrounding the vacuum-activated storage container 1000, such as immediately after placement of the volatile object within the vacuum-activated storage container 1000, the coupling device 1050 provides a holding force to maintain desired positioning of the first shell case side 1010 relative to the second shell case side 1020 such that the interior surfaces of flanges 1014 and 1024 create an air-tight seal therebetween. Once the pressure outside of the vacuum-activated storage container 1000 begins to rise (e.g., when removing the vacuum-activated storage container 1000 from a vacuum environment during transportation), the atmospheric pressure surrounding the vacuum-activated storage container 1000 provides additional holding force to maintain the vacuum-activated storage container 1000 in the sealed configuration. As discussed in greater detail herein, this additional holding force can prevent or impede opening of the vacuum-activated storage container 1000 when in an atmospheric environment in which exposure of the volatile object can result in undesirable reaction with components of atmospheric air.

As shown, the coupling device 1050 can be a ring clamp that can be placed around a perimeter of the shell case assembly. The coupling device 1050 can include a material identical to the material of the first shell case side 1010 and the second shell case side 1020, or the coupling device 1050 can include a material different from the first shell case side 1010 and the second shell case side 1020. As an example, the coupling device 1050 can include a steel material.

The ring clamp of the illustrated embodiment includes a tightening mechanism 1051 that can be tightened to decrease the diameter of ring clamp, thereby tightening the coupling device 1050 onto flanges 1014 and 1024. As noted above, at least in part due to the chamfered exterior surfaces of flanges 1014 and 1024, tightening the ring clamp creates a compressive pressure causing the interior surfaces of flanges 1014 and 1024 to seal relative to one another.

Example Method of Use of a Vacuum-Activated Storage Container

As a method of using the vacuum-activated storage container 1000, the volatile object can be placed into an interior thereof while the vacuum-activated storage container 1000 is in an open configuration with the first shell case side 1010 separated from the second shell case side 1020. In use, the volatile object is placed into the interior of the vacuum-activated storage container 1000 while the volatile object and the vacuum-activated storage container 1000 are positioned within a vacuum environment, such as within a glovebox operated under vacuum pressure.

Specifically, the volatile object is placed into an interior portion of either the first shell case side 1010 or the second shell case side 1020. A surface of the volatile object is in contact with holding member 1030, 1040. The other of the first shell case side or the second shell case side 1020 is provided to enclose the shell case assembly, such that the interior surface of each of the flanges 1014, 1024 is in contact with one another. The other holding member 1030, 1040 contacts the other side of the volatile object, such that the volatile object is positioned between the holding members 1030, 1040.

The coupling device 1050 is then positioned around the perimeter of the shell case assembly and tightened to create force vectors on the flanges 1014 and 1024 compressing the interior surfaces of the flanges 1014 and 1024 relative to one another to create an air-tight seal therebetween. By tightening the coupling device 1050, the holding members 1030, 1040 are additionally compressed against respective surfaces of the volatile device to create a frictional engagement with the volatile device to prevent the volatile device from shifting within the interior of the vacuum-activated storage container 1000. Tightening the coupling device 1050 thereby places the vacuum-activated storage container 1000 in the closed and sealed configuration.

The sealed vacuum-activated storage container 1000 is then removed from the vacuum environment, thereby subjecting the vacuum-activated storage container 1000 to a pressure differential with the pressure external to the vacuum-activated storage container 1000 being higher than the vacuum pressure within the enclosed interior volume of the vacuum-activated storage container 1000. This pressure differential creates an additional holding force sealing the vacuum-activated storage container 1000 in the sealed configuration.

If the sealed vacuum-activated storage container 1000 is subsequently subject to an ambient vacuum environment such that the pressure external to the vacuum-activated storage container 1000 falls below the pressure within the enclosed interior volume of the vacuum-activated storage container 1000 (e.g., by at least 1 mbar), the vacuum-activated check valve 1060 (and vacuum-activated check valve 1070, if present) opens to equalize the pressure within the enclosed interior volume with the exterior of the vacuum-activated storage container 1000.

To open the sealed vacuum-activated storage container 1000, such as when removing an enclosed target device 196 for installation within a target assembly 200, the vacuum-activated storage container 1000 is placed into a vacuum environment, such that the pressure external to the vacuum-activated storage container 1000 is at least substantially equal to the pressure within the enclosed interior volume of the vacuum-activated storage container 1000. The coupling device 1050 is then loosened and removed from the shell case assembly. The first shell case side 1010 is removed from the second shell case side 1020, thereby configuring the vacuum-activated storage container 1000 into the open configuration, exposing the enclosed volatile device, which can then be freely removed, such as for installation into a target assembly 200.

Various aspects of the present subject matter are set forth below, in review of, and/or in supplementation to, the embodiments described thus far, with the emphasis here being on the interrelation and interchangeability of the following embodiments. In other words, an emphasis is on the fact that each feature of the embodiments can be combined with each and every other feature unless explicitly stated otherwise or logically implausible.

A removal system for a radioactive component of a beam system is provided in implementations discussed herein. The beam system includes: a movable device configured to carry a radioactive component, and a guide structure configured to receive the movable device and guide movement of the radioactive component from a first position to a second position. The movable device of example embodiments is configured as a carriage. The carriage can be configured to secure the radioactive component, and the carriage can include one or more wheels (e.g., to ease movement along a guide track). The guide structure is embodied as a guide track in some example implementations. The guide track can include a recessed space configured to hold and permit rotation of a wheel of the movable device.

In some embodiments, the guide structure is configured such that movement of the moveable device along the guide structure changes the position and the orientation of the radioactive component The first position can be an operative position within the beam system, and the second position can be a position within a shielded container.

In many embodiments, a neutron beam system is provided that includes: a target exchange system including a movable device and a guide structure, where the movable device is configured to carry a radioactive target assembly along a guide structure, and where the guide structure is configured to guide movement of the movable device from a beam shaping assembly to a shielded container. In some of these embodiments, the movable device is a carriage including one or more wheels and the guide structure is a track configured to receive the one or more wheels.

In some of these embodiments, the guide structure includes a first straight section, a second straight section, and a third curved section positioned between the first straight section and the second straight section. The first straight section can have a terminus at a beam shaping assembly and can be oriented along a beam axis of the beam system. The second straight section can have a terminus at a space configured to hold a shielded container. The second straight section can be oriented along an axis transverse to the beam-axis of the beam system.

In many embodiments, a method of removing a radioactive component from a beam system is provided, the method including: moving the radioactive component from an operative position in the beam system, along a guide structure, to a position within a shielded container.

In some of these embodiments, the guide structure guides movement of the radioactive component. In some embodiments, moving the radioactive component includes moving the radioactive component from the operative position in an upstream direction. Moving the radioactive component can further include moving the radioactive component through an aperture in a radiation shield. Moving the radioactive component can include moving the radioactive component along a curved section of the guide structure such that the radioactive component changes position and orientation. Moving the radioactive component can further include moving the radioactive component from the curved section to an upper straight section of the guide structure, and then changing the direction of motion to move the radioactive component along the upper straight section a second time. Moving the radioactive component can further include moving the radioactive component from the upper straight section to a lower straight section and into the shielded container.

In some of these embodiments, the movable structure is a carriage including a wheel, and the guide structure is a track configured to receive and permit rotation of the wheel.

In some of these embodiments, the radioactive component is a target assembly configured to generate neutrons when impacted by a proton beam. The beam system of certain embodiments is configured for use with a boron neutron capture therapy (BNCT).

In many embodiments, a removal system for a radioactive component of a beam system is provided, the removal system including: a radioactive component having a first side that is relatively more radioactive than a second side; and a guide structure configured to guide movement of the radioactive component into a shielded container such that the first side enters the shielded container before the second side.

In some embodiments, the radioactive component can be coupled with a movable device configured to move along the guide structure. The movable device can be secured to the radioactive component. The movable device can be secured to the radioactive component. The movable device can be configured as a carriage including at least one wheel. The guide structure can be configured as a track. The track can include a recessed space configured to hold and permit rotation of the at least one wheel of the carriage.

In some embodiments, the guide structure is configured such that movement of the radioactive component along the guide structure changes the position and the orientation of the radioactive component. The guide structure can include a first straight track section, a second straight track section, and a curved track section, where the curved track section is coupled between the first straight track section and the second straight track section. The first straight track section can be oriented along a beam axis of the beam system and the second straight track section is oriented transverse to the beam axis. The second straight track section can be oriented over a space for placement of the shielded container.

In some embodiments, the guide structure can include a first guide section and a second guide section, where the second guide section is configured to pivot with respect to the first guide section. The system can include a releasable lock mechanism configured to lock the second guide section in a position aligned with the first guide section. The system can include a bias member configured to assist a pivot movement of the second guide section. The bias member can be a dampening spring. The system can include an automatic lowering mechanism configured to assist lowering of the radioactive component along the second guide section in a pivoted state.

In some embodiments, the guide structure is configured to move the radioactive component from an operative position within the beam system to a position within the shielded container.

In many embodiments, a target exchange system is provided, the system including: a guide structure configured to interface with a target assembly, the target assembly having a first side with a radioactive target and a second side, where the guide structure is configured to guide movement of the target assembly into a shielded container such that the first side of the target assembly enters the shielded container before the second side.

In some embodiments, the target assembly can be coupled with a movable device configured to move along the guide structure. The movable device can be a carriage including one or more wheels and the guide structure is a track configured to receive the one or more wheels.

In some embodiments, the guide structure can include a first straight section, a second straight section, and a third curved section positioned between the first straight section and the second straight section. The first straight section can have a terminus at a beam shaping assembly and is oriented along a beam axis of the beam system. The second straight section can have a terminus at a space configured to hold a shielded container. The second straight section can be oriented along an axis transverse to the beam axis of the beam system.

In some embodiments, the guide structure can include a first guide section and a second guide section, where the second guide section is configured to pivot with respect to the first guide section. The system can further include a releasable lock mechanism configured to lock the second guide section in a position aligned with the first guide section. The system can further include a bias member configured to assist a pivot movement of the second guide section. The bias member can be a dampening spring. The system can further include an automatic lowering mechanism configured to assist lowering of the radioactive component along the second guide section in a pivoted state.

In some embodiments, the guide structure is configured to move the radioactive component from an operative position within the beam system to a position within the shielded container.

In some embodiments, the system further includes a beamline and the target assembly. The system can include a valve coupled between the beamline and the target assembly. The valve can include a first housing releasably coupled with a second housing, where the first housing is secured to the target assembly and the second housing is secured to the beamline. The valve can include a rotatable or pivotable seal member coupled with the first housing and configured to seal an interior space of the target assembly.

In many embodiments, a method of removing a radioactive component from a beam system is provided, where the radioactive component has a first side that is relatively more radioactive than a second side, the method including: moving the radioactive component from an operative position in the beam system to a position within a shielded container such that the first side enters the shielded container before the second side, where at least a portion of the movement is along a guide structure.

In some embodiments, the guide structure guides movement of the radioactive component.

In some embodiments, moving the radioactive component includes moving the radioactive component from an operative position in an upstream direction along the guide structure.

In some embodiments, moving the radioactive component further includes moving the radioactive component through an aperture in a radiation shield.

In some embodiments, moving the radioactive component further includes moving the radioactive component along a curved section of the guide structure such that the radioactive component changes position and orientation. Moving the radioactive component can further include moving the radioactive component from the curved section to an upper straight section of the guide structure, and then changing the direction of motion to move the radioactive component along the upper straight section a second time. Moving the radioactive component can further include moving the radioactive component from the upper straight section to a lower straight section and into the shielded container.

In some embodiments, moving the radioactive component further includes: moving the radioactive component along a first guide section to a second guide section, and pivoting the second guide section such that the radioactive component also pivots. The method can further include unlocking the second guide section prior to pivoting the second guide section. The second guide section and the radioactive component can be pivoted with the assistance of a bias member. The bias member can be a dampening spring.

In some embodiments, the method can further include moving the pivoted radioactive component along the pivoted second guide section and into the shielded container.

In some embodiments, the method can further include moving the pivoted radioactive component along the pivoted second guide section and into the shielded container at least partially with an automated lowering mechanism.

In some embodiments, the method can further include inserting a replacement component into the first guide section.

In some embodiments, the movable structure is a carriage including a wheel, and the guide structure is a track configured to receive and permit rotation of the wheel.

In some of these embodiments, the radioactive component is a target assembly configured to generate neutrons when impacted by a proton beam.

In some of these embodiments, the beam system is configured for use in a BNCT.

In many embodiments, a method of removing a radioactive target assembly from a neutron beam system is provided, the method including: moving the target assembly along a guide structure; pivoting a portion of the guide structure and the target assembly; and moving the pivoted target assembly into a shielded container.

In some embodiments, the method further includes: decoupling the target assembly from a section of a beamline; and removing the section of the beamline. Decoupling the target assembly from the section of the beamline can include releasing a lock mechanism on a valve assembly. The method can further include closing the valve assembly prior to decoupling the target assembly from the section of the beamline. The valve assembly can be closed by rotating or pivoting a seal member.

In some of these embodiments, the portion is a section portion and moving the target assembly along the guide structure includes: moving the target assembly from proximity with a beam shaping apparatus along a first portion of the guide structure through an aperture in a retractable radiation shield to the second portion of the guide structure. The target assembly can be moved from the first portion to the second portion of the guide structure without retraction of the radiation shield. The garget assembly can include a valve that is moved through the aperture in the retractable radiation shield.

In some of these embodiments, the method further includes moving the pivoted target assembly into a shielded container with the assistance of an automated lowering mechanism.

In some of these embodiments, the method further includes sealing the shielded container with the target assembly contained therein.

In some of these embodiments, the target assembly has a radioactive target located at a downstream end of the target assembly, and where the downstream end of the target assembly is oved into the shielded container before an upstream end of the target assembly.

In many embodiments, a facility is provided, the facility including: a neutron beam system including a target assembly; a beam shaping apparatus configured to receive the target assembly; a retractable radiation shield having an aperture through which the target assembly can pass; and a target exchange system configured to facilitate removal of the target assembly without retraction of the radiation shield.

In some embodiments, the neutron beam system further includes: an ion source; a first beamline coupled with the ion source; an accelerator coupled with the first beamline; and a second beamline coupled between the accelerator and the target assembly. The second beamline can include a removable section coupled with the target assembly. The neutron beam system can further include a valve assembly having a first housing that releasably couples with a second housing, where the first housing is secured to the target assembly and the second housing is secured to the removable section. The valve assembly can include a rotatable or pivotable seal. The valve assembly can include a releasable lock mechanism for releasably coupling the first housing with the second housing. The valve assembly can be sized to pass through the aperture in the radiation shield.

In some embodiments, the retractable radiation shield includes a first shield door and a second shield door, where the aperture is formed by the interface between the first and second shield doors.

In some of these embodiments, the target exchange system is configured in accordance with any of the embodiments described herein.

In some of these embodiments, the target exchange system has a support structure with a first portion located between the beam shaping assembly and a first die of the radiation shield, and a second portion located on a second side of the radiation shield.

In many embodiments, a valve assembly is provided, the valve assembly including: a seal member; a first housing coupled with the seal member; a second housing configured to couple with the first housing; and a releasable lock mechanism configured to releasably lock the first housing to the second housing, where the seal member is configured to pivot or rotate from an open position to a closed position, and where the valve assembly is configured to permit the passage of a charged particle beam therethrough when the seal member is in the open position. In some of these embodiments, the valve assembly further includes an actuator for manual actuation of the seal member. The actuator can be a rotatable lever or crank. In some of these embodiments, the valve assembly further includes an actuator for automatic actuation of the seal member.

In some of these embodiments, both of the first housing includes an interface for a gas impermeable seal, with a target assembly of a neutron beam system, in the second housing includes an interface for a gas impermeable seal with a beamline of the neutron beam system.

In some of these embodiments, the valve assembly further includes a port for pressurization or depressurization of an interior space of the valve assembly.

In various embodiments, a shielded container for storing a radioactive component includes an inner container shell having multiple inner shell walls collectively defining a first hollow interior for housing the radioactive component, and an outer container shell having multiple outer shell walls collectively defining a second hollow interior for housing the inner container shell.

In some of these embodiments, the multiple inner shell walls each include at least one gamma shielding material and the multiple outer shell walls each include at least one gamma shielding material. In some of these embodiments, the at least one gamma shielding material includes one or more of bismuth, iron, nickel, lead, depleted uranium, aluminum, or copper.

In some of these embodiments, the inner container shell further defines an open end and the inner container shell further includes a door assembly configurable between an open configuration providing access to the first hollow interior of the inner container shell and a closed configuration preventing access to the first hollow interior of the inner container shell.

In some of these embodiments, the outer container shell further defines an open end and the outer container shell further includes a door assembly configurable between an open configuration providing access to the second hollow interior of the outer container shell, and a closed configuration preventing access to the second hollow interior of the outer container shell. In some of these embodiments, the door assembly of the outer container shell includes a mechanical linkage operable to move a door between the open configuration and the closed configuration. In some of these embodiments, the door assembly includes at least one gamma shielding material. In some of these embodiments, the at least one gamma shielding material includes one or more of bismuth, iron, nickel, lead, depleted uranium, aluminum, or copper.

In some of these embodiments, the mechanical linkage includes a handle. In some of these embodiments, the mechanical linkage defines at least two pivot points. In some of these embodiments, the mechanical linkage is a five-bar linkage. In some of these embodiments, the door assembly includes a locking mechanism configured to selectively lock the door assembly in the closed configuration.

In some of these embodiments, the shielded container further includes an interim shell having multiple interim shell walls collectively defining a third hollow interior for housing the inner container shell. In some of these embodiments, the outer container shell is configured to house the interim shell within the second hollow interior of the outer container shell.

In some of these embodiments, the inner shell walls define a variable thickness profile defining a first portion of the inner shell walls having a first thickness and a second portion of the inner shell walls having a second thickness. In some of these embodiments, the first thickness is greater than the second thickness.

In some of these embodiments, the outer shell walls define a variable thickness profile defining a first portion of the outer shell walls having a first thickness and a second portion of the outer shell walls having a second thickness. In some of these embodiments, the first thickness is greater than the second thickness.

In some of these embodiments, the multiple interim shell walls define a variable thickness profile defining a first portion of the interim shell walls having a first thickness and a second portion of the interim shell walls having a second thickness. In some of these embodiments, the first thickness is greater than the second thickness.

In various embodiments, a method of storing a radioactive component includes placing the radioactive component into an inner container shell having multiple inner shell walls collectively defining a first interior for housing the radioactive component. In some of these embodiments, the inner container shell is positioned within an outer container shell having multiple outer shell walls collectively defining a second interior for housing the inner container shell. In some of these embodiments, the method further includes closing the inner container shell and the outer container shell.

In some of these embodiments, the method further includes, after the radioactive component decays for a period of time, opening the outer container shell. In some of these embodiments, the method further includes removing the inner container shell from the outer container shell. In some of these embodiments, each of the outer container shell and the inner container shell include at least one gamma shielding material.

In some of these embodiments, the at least one gamma shielding material includes one or more of bismuth, iron, nickel, lead, depleted uranium, aluminum, or copper.

In some of these embodiments, closing the inner container shell and the outer container shell includes moving a handle of the outer container shell from a first position to a second position. In some of these embodiments, the handle of the outer container shell is a part of a mechanical linkage. In some of these embodiments, moving the handle from the first position to the second position moves a door of the outer container shell from an open configuration to a closed configuration.

In some of these embodiments, closing the inner container shell and the outer container shell includes rotating a drive key. In some of these embodiments, the drive key is connected in a gearing relationship with a door of the outer container shell such that rotation of the drive key moves the door of the outer container shell from the open configuration to the closed configuration.

In some of these embodiments, the inner container shell is positioned within an interim container shell and the interim container shell is positioned within the outer container shell, and further including closing the interim container shell.

In some of these embodiments, the method further includes, after the radioactive component decays for a first period of time, opening the outer container shell. In some of these embodiments, the method further includes removing the interim container shell from the outer container.

In some of these embodiments, the method further includes, after the radioactive component decays for a second period of time occurring consecutively with the first period of time, opening the interim container shell. In some of these embodiments, the method further includes removing the inner container shell from the interim container shell. In some of these embodiments, each of the outer container shell, the interim container shell, and the inner container shell includes at least one gamma shielding material. In some of these embodiments, the at least one gamma shielding material includes one or more of bismuth, iron, nickel, lead, depleted uranium, aluminum, or copper.

In some of these embodiments, placing the radioactive component into the inner container shell includes guiding the radioactive component into the inner container shell along a guide structure.

In various embodiments, a removal system for a radioactive component of a beam system includes a radioactive component and a shielded container including an inner container shell having multiple inner shell walls collectively defining a first hollow interior for housing the radioactive component, and an outer container shell having multiple outer shell walls collectively defining a second hollow interior for housing the inner container shell. In some of these embodiments, the removal system further includes a guide structure configured to guide movement of the radioactive component into the first hollow interior of the inner container shell of the shielded container.

In some of these embodiments, the radioactive component is coupled with a movable device configured to move along the guide structure.

In some of these embodiments, the guide structure is configured as a track.

In some of these embodiments, the guide structure is configured such that movement of the radioactive component along the guide structure changes a position and orientation of the radioactive component.

In some of these embodiments, the guide structure includes a first straight track section, a second straight track section, and a curved track section. In some of these embodiments, the first straight track section is oriented along a beam axis of the beam system, the second straight track section is oriented over the shielded container and is oriented transverse to the beam axis, and the curved track section is coupled between the first straight track section and the second straight track section.

In some of these embodiments, the guide structure is configured to move the radioactive component from an operative position within the beam system to a position within the first hollow interior of the inner container shell of the shielded container.

In some of these embodiments, the shielded container further includes an interim shell having multiple interim shell walls collectively defining a third hollow interior for housing the inner container shell. In some of these embodiments, the outer container shell is configured to house the interim shell within the second hollow interior of the outer container shell.

In some of these embodiments, the inner shell walls define a variable thickness profile defining a first portion of the inner shell walls having a first thickness and a second portion of the inner shell walls having a second thickness. In some of these embodiments, the first thickness is greater than the second thickness.

In some of these embodiments, the outer shell walls define a variable thickness profile defining a first portion of the outer shell walls having a first thickness and a second portion of the outer shell walls having a second thickness. In some of these embodiments, the first thickness is greater than the second thickness.

In some of these embodiments, the interim shell walls define a variable thickness profile defining a first portion of the interim shell walls having a first thickness and a second portion of the interim shell walls having a second thickness. In some of these embodiments, the first thickness is greater than the second thickness.

In some of these embodiments, each of the outer container shell and the inner container shell includes at least one gamma shielding material.

In some of these embodiments, the at least one gamma shielding material includes one or more of bismuth, iron, nickel, lead, depleted uranium, aluminum, or copper.

In various embodiments, a target exchange system includes a shielded container including an inner container shell having multiple inner shell walls collectively defining a first hollow interior for housing the radioactive component and an outer container shell having multiple outer shell walls collectively defining a second hollow interior for housing the inner container shell. In some of these embodiments, the shielded container further includes a guide structure configured to interface with a target assembly. In some of these embodiments, the guide structure is configured to guide movement of the target assembly into the first hollow interior of the inner container of the shielded container.

In some of these embodiments, the guide structure includes a first straight section, a second straight section, and a third curved section positioned between the first and second sections.

In some of these embodiments, the first straight section is oriented along a beam axis of the beam system, the second straight section is oriented over the shielded container and is oriented transverse to the beam axis, and the curved track section is coupled between the first straight section and the second straight section.

In some of these embodiments, the guide structure is configured to move the radioactive component from an operative position within a beam system to a position within the first hollow interior of the inner container shell of the shielded container.

In some of these embodiments, the shielded container further includes an interim shell having multiple interim shell walls collectively defining a third hollow interior for housing the inner container shell. In some of these embodiments, the outer container shell is configured to house the interim shell within the second hollow interior of the outer container shell.

In some of these embodiments, the inner shell walls define a variable thickness profile defining a first portion of the inner shell walls having a first thickness and a second portion of the inner shell walls having a second thickness. In some of these embodiments, the first thickness is greater than the second thickness.

In some of these embodiments, the outer shell walls define a variable thickness profile defining a first portion of the outer shell walls having a first thickness and a second portion of the outer shell walls having a second thickness. In some of these embodiments, the first thickness is greater than the second thickness.

In some of these embodiments, the interim shell walls define a variable thickness profile defining a first portion of the interim shell walls having a first thickness and a second portion of the interim shell walls having a second thickness. In some of these embodiments, the first thickness is greater than the second thickness.

In some of these embodiments, each of the outer container shell and the inner container shell includes at least one gamma shielding material.

In some of these embodiments, the at least one gamma shielding material includes one or more of bismuth, iron, nickel, lead, depleted uranium, aluminum, or copper.

In various embodiments, a storage container for storing a volatile object includes a shell case assembly including a first shell case side and a second shell case side. In some of these embodiments, the shell case assembly defines an exterior surface and an enclosed interior volume defined within an interior portion of each of the first shell case side and the second shell case side and configured for housing a volatile object. In some of these embodiments, the first shell case side is configured to engage the second shell case side to form a gas seal therebetween. IN some of these embodiments, the enclosed interior is at a first atmospheric pressure lower than a second atmospheric pressure exterior to the enclosed interior volume. The first atmospheric pressure of some embodiments is a vacuum pressure and the second atmospheric pressure is ambient pressure exterior to the enclosed interior volume. In some of these embodiments, the storage container further includes a coupling device configured to secure the first shell case side with the second shell case side. In some of these embodiments, the first shell case side includes a check valve extending therethrough. In some of these embodiments, the check valve is configured to open with a lower pressure at the exterior surface of the first shell case side than a pressure at the interior portion of the first shell case side. In some embodiments, the check valve is a vacuum-activated check valve.

In some of these embodiments, the first shell case side defines a first flange extending around a perimeter of the first shell case side and the second shell case side defines a second flange extending around a perimeter of the second shell case side. In some of these embodiments, the first flange is configured to engage the second flange to form the gas seal between the first shell case side and the second shell case side.

In some of these embodiments, the second shell case side includes a second check valve extending therethrough. In some of these embodiments, the second check valve is configured to open with a lower pressure at the exterior surface of the second shell case side.

In some of these embodiments, the first shell case side additionally includes a holding member secured onto an interior surface within the interior portion of the first shell case side. In some of these embodiments, the holding member is configured to frictionally engage a surface of the volatile object.

In some of these embodiments, the second shell case side additionally includes a second holding member secured onto an interior surface within the interior portion of the second shell case side. In some of these embodiments, the second holding member is configured to frictionally engage a second surface of the volatile object.

In some of these embodiments, the holding member is an O-ring seated within a channel defined within the interior surface of the first shell case side.

In some of these embodiments, the shell case assembly has an at least substantially circular perimeter, and the coupling device is a ring clamp configured to extend around the at least substantially circular perimeter of the shell case assembly.

In some of these embodiments, the shell case assembly includes aluminum.

In some of these embodiments, the check valve is configured to open upon a pressure at the exterior surface of the first shell case side being at least 1 mbar lower than a pressure within the enclosed interior volume.

In some of these embodiments, the first shell case side is identical to the second shell case side.

In some of these embodiments, the shell case assembly is configurable between a closed configuration in which the first shell case side is engaged with the second shell case side to form a gas seal therebetween, and an open configuration in which the first shell case side is separated from the second shell case side to access from an exterior of the storage container into the enclosed interior volume.

In some of these embodiments, the first shell case side is movably secured to the second shell case side in the open configuration.

In various embodiments, a packaged volatile object includes a shell case assembly including a first shell case side and a second shell case side. In some of these embodiments, the shell case assembly defines an exterior surface and an enclosed interior volume defined within an interior portion of each of the first shell case side and the second shell case side. In some of these embodiments, the first shell case side is configured to engage the second shell case side to form a gas seal therebetween. In some of these embodiments, the packaged volatile object further includes a volatile object positioned within the enclosed interior volume. In some of these embodiments, the enclosed interior volume is at a vacuum pressure. In some of these embodiments, the first shell case side includes a check valve extending therethrough. In some of these embodiments, the check valve is configured to open with a lower pressure at the exterior surface of the first shell case side.

In some of these embodiments, the packaged volatile object further includes a coupling device configured to secure the first shell case side with the second shell case side.

In some of these embodiments, the first shell case side defines a first flange extending around a perimeter of the first shell case side and the second shell case side defines a second flange extending around a perimeter of the second shell case side. In some of these embodiments, the first flange is configured to engage the second flange to form the gas seal between the first shell case side and the second shell case side.

In some of these embodiments, the second shell case side includes a second check valve extending therethrough. In some of these embodiments, the second check valve is configured to open with a lower pressure at the exterior surface of the second shell case side.

In some of these embodiments, the first shell case side additionally includes a holding member secured onto an interior surface within the interior portion of the first shell case side. In some of these embodiments, the holding member is configured to frictionally engage a surface of the volatile object.

In some of these embodiments, the second shell case side additionally includes a second holding member secured onto an interior surface within the interior portion of the second shell case side. In some of these embodiments, the second holding member is configured to frictionally engage a second surface of the volatile object.

In some of these embodiments, the holding member is an O-ring seated within a channel defined within the interior surface of the first shell case side.

In some of these embodiments, the shell case assembly has an at least substantially circular perimeter, and the coupling device is a ring clamp configured to extend around the at least substantially circular perimeter of the shell case assembly.

In some of these embodiments, the volatile object has an at least substantially circular perimeter.

In some of these embodiments, the shell case assembly includes aluminum.

In some of these embodiments, the check valve is configured to open upon a pressure at the exterior surface of the first shell case side being at least 1 mbar lower than a pressure within the enclosed interior volume.

In some of these embodiments, the first shell case side is identical to the second shell case side.

In some of these embodiments, the shell case assembly is configurable between a closed configuration in which the first shell case side is engaged with the second shell case side to form a gas seal therebetween, and an open configuration in which the first shell case side is separated from the second shell case side to access the volatile object from an exterior of the shell case assembly.

In some of these embodiments, the volatile object includes a metal disk and a volatile composition coated onto a first side of the metal disk. In some of these embodiments, the metal disk includes copper.

In some of these embodiments, the volatile composition includes one of: lithium, sodium, or magnesium.

In some of these embodiments, the volatile object is configured to produce a neutron beam when impacted by a beam of energetic protons.

In various embodiments, a method of storing a volatile object includes placing the volatile object into an interior portion of one of a first shell case side or a second shell case side while the volatile object, the first shell case side, and the second shell case side are in an environment with a first pressure. In some of these embodiments, the first shell case side includes a check valve extending therethrough. In some of these embodiments, the check valve is configured to open with a lower pressure at an exterior surface of the first shell case side than a pressure at the interior portion of the first shell case side. In some of these embodiments, the method further includes forming a closed shell case assembly around the volatile object by engaging the first shell case side with the second shell case side and thereby forming an enclosed interior volume housing the volatile object within the closed shell case assembly. In some of these embodiments, the method further includes securing a coupling device to the closed shell case assembly to secure the first shell case side with the second shell case side. In some of these embodiments, the method further includes subjecting the closed shell case assembly to an a second pressure greater than the first pressure to cause the first shell case side to form a gas seal with the second shell case side.

In some of these embodiments, the method further includes, after subjecting the closed shell case assembly to the second pressure, subjecting the closed shell case assembly to a third pressure that is at least 1 mbar lower than the first pressure within the enclosed interior volume to open the check valve to equalize the first pressure within the enclosed interior volume with the third pressure via the check valve. In some embodiments, the check valve is a vacuum-activated check valve and the first pressure is a vacuum pressure.

In some of these embodiments, the second shell case side includes a second check valve extending therethrough. In some of these embodiments, the second check valve is configured to open with a lower pressure at the exterior surface of the second shell case side. In some of these embodiments, subjecting the closed shell case assembly to a vacuum pressure in which the vacuum pressure is at least 1 mbar lower than a pressure within the enclosed interior volume additionally opens the second check valve to equalize the pressure within the enclosed interior volume with the vacuum pressure via the check valve and the second check valve.

In some of these embodiments, one of the first shell case side or the second shell case side additionally includes a holding member secured onto an interior surface within the interior portion of the first shell case side or the second shell case side. In some of these embodiments, forming the closed shell case assembly includes frictionally engaging the holding member with a surface of the volatile object.

In some of these embodiments, both of the first shell case side and the second shell case side additionally includes a holding member secured onto an interior surface within the interior portion of the first shell case side and the second shell case side. In some of these embodiments, forming the closed shell case assembly includes frictionally engaging the holding member of the first shell case side with a first surface of the volatile object and frictionally engaging the holding member of the second shell case side with a second surface of the volatile object.

In some of these embodiments, the first shell case side defines a first flange extending around a perimeter of the first shell case side and the second shell case side defines a second flange extending around a perimeter of the second shell case side. In some of these embodiments, forming a closed shell case assembly includes engaging the first flange with the second flange to form the gas seal between the first shell case side and the second shell case side.

In various embodiments, a package includes a shell case assembly including a first shell case side and a second shell case side. In some of these embodiments, the shell case assembly defines an exterior surface and an enclosed interior volume defined within an interior portion of each of the first shell case side and the second shell case side. In some of these embodiments, the first shell case side is configured to engage the second shell case side to form a gas seal therebetween. In some of these embodiments, the enclosed interior volume is at a first atmospheric pressure lower than a second atmospheric pressure exterior to the enclosed interior volume.

In some of these embodiments, the first shell case side includes a check valve extending therethrough. In some of these embodiments, the check valve is configured to open with a lower pressure at the exterior surface of the first shell case side. In some of these embodiments, the first atmospheric pressure is vacuum pressure and the second atmospheric pressure is ambient pressure exterior to the enclosed interior volume.

In some of these embodiments, the package includes a coupling device configured to secure the first shell case side with the second shell case side. In some embodiments, the first shell case side defines a first flange extending around a perimeter of the first shell case side and the second shell case side defines a second flange extending around a perimeter of the second shell case side. In some of these embodiments, the first flange is configured to engage the second flange to form the gas seal between the first shell case side and the second shell case side.

In some of these embodiments, the second shell case side includes a second check valve extending therethrough. In some of these embodiments, the second check valve is configured to open with a lower pressure at the exterior surface of the second shell case side.

In some of these embodiments, the first shell case side includes a holding member secured onto an interior surface within the interior portion of the first shell case side. In some of these embodiments, the holding member is configured to frictionally engage a surface of a volatile object. In some of these embodiments, the second shell case side includes a second holding member secured onto an interior surface within the interior portion of the second shell case side. In some of these embodiments, the second holding member is configured to frictionally engage a second surface of the volatile object. In some embodiments, the holding member is an O-ring seated within a channel defined within the interior surface of the first shell case side.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

As used herein and in the appended claims, the singular forms "a," "an," and "the" include plural referents unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. A shielded container for storing a radioactive component, the shielded container comprising:
    an inner container shell having a plurality of inner shell walls and a first door assembly configurable between:
        an open configuration providing access to a first hollow interior of the inner container shell for housing the radioactive component; and
        a closed configuration in which the first door assembly contacts at least one of the plurality of inner shell walls to seal and prevent access to the first hollow interior, wherein the at least one of the plurality of inner shell walls that contacts the first door assembly in the closed configuration comprises at least one gamma shielding material; and
    an outer container shell having a plurality of outer shell walls comprising at least one gamma shielding material and a second door assembly collectively defining a second hollow interior for housing the inner container shell;
    wherein the second door assembly is operable between an open configuration and a closed configuration while the first door assembly is in the closed configuration.

2. The shielded container of claim 1, wherein the at least one gamma shielding material comprises one or more of bismuth, iron, nickel, lead, depleted uranium, aluminum, or copper.

3. The shielded container of claim 1, wherein the outer container shell further defines an open end and the second door assembly configurable between:
    the open configuration providing access to the second hollow interior of the outer container shell; and
    the closed configuration preventing access to the second hollow interior of the outer container shell.

4. The shielded container of claim 3, wherein the second door assembly of the outer container shell comprises a mechanical linkage operable to move a door of the outer container shell between the open configuration and the closed configuration.

5. The shielded container of claim 4, wherein the second door assembly comprises at least one gamma shielding material.

6. The shielded container of claim 5, wherein the at least one gamma shielding material comprises one or more of bismuth, iron, nickel, lead, depleted uranium, aluminum, or copper.

7. The shielded container of claim 4, wherein the mechanical linkage comprises a handle.

8. The shielded container of claim 4, wherein the mechanical linkage defines at least two pivot points.

9. The shielded container of claim 4, wherein the mechanical linkage is a five-bar linkage.

10. The shielded container of claim 4, wherein the second door assembly comprises a locking mechanism configured to selectively lock the second door assembly in the closed configuration.

11. The shielded container of claim 4, wherein the mechanical linkage comprises multiple bars pivotably secured to the door of the outer container shell at a first end of each of the multiple bars and pivotably secured at pivot points of the outer container shell at second ends of each of the multiple bars, and wherein the mechanical linkage is configured to maintain a parallel alignment between the door of the outer container shell and the open end during movement between the open configuration and the closed configuration.

12. The shielded container of claim 11, wherein the mechanical linkage is a second mechanical linkage and comprises a handle to actuate movement of the second mechanical linkage, and wherein the first door assembly of the inner container shell comprises a first mechanical linkage operable to move a door of the inner container shell between an open configuration and a closed configuration, and
wherein the first mechanical linkage is positioned within the second hollow interior and operably connected with the second mechanical linkage while the inner container shell is positioned within the second hollow interior such that actuation of movement of the second mechanical linkage by the handle causes movement of the first mechanical linkage.

13. The shielded container of claim 1, further comprising an interim shell having a plurality of interim shell walls collectively defining a third hollow interior for housing the inner container shell, and wherein the outer container shell is configured to house the interim shell within the second hollow interior of the outer container shell.

14. The shielded container of claim 13, wherein the plurality of interim shell walls define a variable thickness profile defining a first portion of the plurality of interim shell walls having a first thickness and a second portion of the plurality of interim shell walls having a second thickness, wherein the first thickness is greater than the second thickness.

15. The shielded container of claim 14, wherein the variable thickness profile is defined by an interim shell wall thickness that varies based on a proximity to a target of the radioactive component.

16. A shielded container for storing a radioactive component, the shielded container comprising:
an inner container shell having a plurality of inner shell walls and a first door assembly collectively defining a first hollow interior for housing the radioactive component; and
an outer container shell having a plurality of outer shell walls and a second door assembly collectively defining a second hollow interior for housing the inner container shell; and
wherein one of:
the plurality of inner shell walls define a variable thickness profile defining a first portion of the plurality of inner shell walls having a first thickness and a second portion of the plurality of inner shell walls having a second thickness, wherein the first thickness is greater than the second thickness; or
the plurality of outer shell walls define a variable thickness profile defining a first portion of the plurality of outer shell walls having a first thickness and a second portion of the plurality of outer shell walls having a second thickness, wherein the first thickness is greater than the second thickness.

17. The shielded container of claim 16, wherein the plurality of inner shell walls define the variable thickness profile and wherein the variable thickness profile is defined by an inner shell wall thickness that varies based on a proximity to a target of the radioactive component.

18. The shielded container of claim 16, wherein the plurality of outer shell walls define the variable thickness profile and wherein the variable thickness profile is defined by an outer shell wall thickness that varies based on a proximity to a target of the radioactive component.

19. A method of storing a radioactive component, the method comprising:
placing the radioactive component into an inner container shell having a plurality of inner shell walls and a first door assembly in an open configuration providing access to a first hollow interior for housing the radioactive component;
moving the first door assembly to a closed configuration in which the first door assembly contacts at least one of the plurality of inner shell walls to seal and prevent access to the first hollow interior, wherein the at least one of the plurality of inner shell walls contacting the first door assembly comprises at least one gamma shielding material, wherein the inner container shell is positioned within an outer container shell having a plurality of outer shell walls comprising at least one gamma shielding material and a second door assembly collectively defining a second interior for housing the inner container shell, wherein the second door assembly is operable between an open configuration and a closed configuration while the first door assembly is in the closed configuration; and
closing the outer container shell.

20. The method of storing a radioactive component of claim 19, wherein:
the first door assembly comprises a first mechanical linkage operable to move a door of the inner container shell between an open configuration and a closed configuration to close the inner container shell;
the second door assembly comprises a second mechanical linkage operable to move a door of the outer container shell relative to an open end of the outer container shell between an open configuration and a closed configuration to close the outer container shell, wherein the second mechanical linkage is configured to maintain a parallel alignment between the door of the outer container shell and the open end while closing the outer container shell; and
wherein the first mechanical linkage is operably connected with the second mechanical linkage, such that closing the inner container shell and closing the outer container shell are performed by actuating the second mechanical linkage.

* * * * *